(12) United States Patent
Beydaghyan et al.

(10) Patent No.: US 11,788,957 B2
(45) Date of Patent: *Oct. 17, 2023

(54) METHOD AND SYSTEM FOR ANALYZING A SAMPLE DESORBED AT DIFFERENT TEMPERATURES USING CAVITY RING-DOWN SPECTROSCOPY, AND A METHOD FOR GENERATING A PREDICTIVE MODEL

(71) Applicant: Picomole Inc., Moncton (CA)

(72) Inventors: Gisia Beydaghyan, Moncton (CA); Christopher Quentin Purves, Moncton (CA); Stephen Douglas Graham, Bedford (CA); Erik Justin Scheme, Hanwell (CA); Angkoon Phinyomark, Douglas (CA)

(73) Assignee: Picomole Inc., Moncton (CA)

(*) Notice: Subject to any disclaimer, the term of this patent is extended or adjusted under 35 U.S.C. 154(b) by 6 days.

This patent is subject to a terminal disclaimer.

(21) Appl. No.: 17/443,873

(22) Filed: Jul. 28, 2021

(65) Prior Publication Data

US 2021/0356392 A1 Nov. 18, 2021

Related U.S. Application Data

(63) Continuation of application No. 16/740,026, filed on Jan. 10, 2020, now Pat. No. 11,105,739.

(Continued)

(51) Int. Cl.
*G01N 21/39* (2006.01)
*G01N 33/497* (2006.01)
(Continued)

(52) U.S. Cl.
CPC ............ *G01N 21/39* (2013.01); *G01J 3/0205* (2013.01); *G01J 3/10* (2013.01); *G01J 3/42* (2013.01);
(Continued)

(58) Field of Classification Search
CPC .......... G01N 21/39; G01N 1/40; G01N 21/31; G01N 21/3504; G01N 21/552;
(Continued)

(56) References Cited

U.S. PATENT DOCUMENTS

2012/0183949 A1* 7/2012 Hyde ..................... B82Y 15/00
977/773

FOREIGN PATENT DOCUMENTS

WO WO-2014062392 A1 * 4/2014 ............. A61B 5/082

* cited by examiner

*Primary Examiner* — Michael A Lyons
*Assistant Examiner* — Omar H Nixon
(74) *Attorney, Agent, or Firm* — Ridout & Maybee LLP

(57) ABSTRACT

Methods and systems for analyzing a sample and generating a predictive model using cavity ring-down spectroscopy are disclosed. At least part of a sample is loaded in a ring-down cavity. For each of a set of wavelengths, a laser beam is generated and directed into the ring-down cavity. The laser beam entering the ring-down cavity is extinguished. Light intensity decay data for light exiting the ring-down cavity is registered via a light intensity sensor system. A probability is determined from the light intensity decay data for the set of wavelengths that a subject from which the sample was received has a physiological condition or a degree of the physiological condition at least indirectly using a dataset of light intensity decay data for previously analyzed samples for which the presence or the absence of the physiological condition or the degree of the physiological condition have been identified.

17 Claims, 7 Drawing Sheets

Related U.S. Application Data

(60) Provisional application No. 62/828,750, filed on Apr. 3, 2019.

(51) Int. Cl.
| | | |
|---|---|---|
| *G01N 1/40* | (2006.01) | |
| *G01J 3/42* | (2006.01) | |
| *G01N 21/3504* | (2014.01) | |
| *G01N 21/552* | (2014.01) | |
| *G01J 3/02* | (2006.01) | |
| *G01N 21/31* | (2006.01) | |
| *G01J 3/10* | (2006.01) | |
| G06N 20/00 | (2019.01) | |
| G01N 21/77 | (2006.01) | |

(52) U.S. Cl.
CPC ............... *G01N 1/40* (2013.01); *G01N 21/31* (2013.01); *G01N 21/3504* (2013.01); *G01N 21/552* (2013.01); *G01N 33/497* (2013.01); *G01J 2003/423* (2013.01); *G01N 2021/391* (2013.01); *G01N 2021/398* (2013.01); *G01N 2021/7789* (2013.01); *G01N 2033/4975* (2013.01); *G06N 20/00* (2019.01)

(58) Field of Classification Search
CPC ........... G01N 33/497; G01N 2021/391; G01N 2021/398; G01N 2021/7789; G01N 2033/4975; G06N 20/00; G01J 3/0205; G01J 3/10; G01J 3/42; G01J 2003/423
USPC ....................................................... 356/451
See application file for complete search history.

METHOD AND SYSTEM FOR ANALYZING A SAMPLE DESORBED AT DIFFERENT TEMPERATURES USING CAVITY RING-DOWN SPECTROSCOPY, AND A METHOD FOR GENERATING A PREDICTIVE MODEL

CROSS-REFERENCE TO RELATED APPLICATIONS

This application is a continuation of U.S. patent application Ser. No. 16/740,026, filed Jan. 10, 2020, which claims the benefit of U.S. Provisional Application No. 62/828,750, filed Apr. 3, 2019, the contents of all of which are incorporated herein by reference in their entirety.

FIELD

The specification relates generally to spectroscopy, and, in particular, to a method and system for analyzing a sample using cavity ring-down spectroscopy, and a method for generating a predictive model.

BACKGROUND OF THE DISCLOSURE

The diagnosis of certain physiological conditions can be challenging. One such physiological condition is lung cancer that is amongst the most prevalent and deadliest forms of cancer. While the prognosis can be improved when lung cancer is discovered in its early, localized stage, most cases are diagnosed when the cancer has already started to spread. Survival rates for lung cancer significantly decline as it spreads from a localized instance to other regions. For this reason, early detection of lung cancer is critical.

Currently, low-dose computed tomography ("LDCT") is recommended to screen for lung cancer. However, this approach is linked with a high false positive rate, resulting in many patients being subjected to unnecessary follow-up evaluations. Along with the high expenses associated with the technology and the patients' exposure to radiation, its lack of sensitivity makes LDCT an unattractive solution as its low specificity can lead to a high false-positive rate.

The abundance of recent research regarding breath biomarkers for lung cancer detection shows promise for this alternate form of screening. Thousands of volatile organic compounds ("VOCs") have been identified in exhaled human breath, ranging in concentrations from parts per million by volume (ppmv) to parts per trillion by volume (pptv). While there is a belief that cancerous cells influence the production of a set of VOCs in the body that can travel through the bloodstream, into the lungs, and out of the body in exhaled breath, there is no strong agreement on what this particular set of VOCs is.

The most widely used technique for VOC detection in exhaled breath is mass spectrometry, which is commonly combined with gas chromatography ("GC-MS"). GC-MS is popular because it offers high selectivity and sensitivity in compound detection and strong accuracy in compound identification. The likelihood that two compounds would behave similarly in both the mass spectrometer and the gas chromatograph is low, making GC-MS a reliable choice when certainty is essential. In lung cancer breath analysis, the earliest use of GC-MS for analyzing lung cancer breath biomarkers was in 1985. Several studies have since followed, collectively identifying dozens of potential biomarkers. Despite the progress made with this technique, GC-MS is impractical for widespread clinical use because it is expensive, time-consuming, and requires complex procedures for sample collection, limiting its applications to laboratory research.

Another technology emerging in breath analysis is the electronic nose ("E-nose"), which uses an array of gas-sensitive sensors to detect different groups of VOCs. This method of VOC detection has some advantages over GC-MS, like its relatively low cost, small size, speed, and ability to be used in "online" applications. Online breath analysis has the potential to eliminate the need for sample storage and provide more immediate feedback to clinicians. However, E-noses are far from ideal. They require frequent calibration, they are sensitive to humidity and temperature changes, and they experience drifting and memory effects. They also tend to lack the features that make GC-MS attractive, like its high sensitivity, high selectivity and its ability to identify individual compounds.

Cavity ring-down spectroscopy ("CRDS") is an approach that is generally used to analyze a sample via its absorption spectra. A typical CRDS system employs a laser generating a beam that is directed into a cavity of a chamber having two highly reflective mirrors. The beam is normally within the visible light spectrum, or the near infrared ("IR") spectrum, and is tuned to a single wavelength. The beam is then reflected repeatedly between the mirrors, which allow a fraction of the light to escape the ring-down cavity.

In order to "fill" the ring-down cavity, the length of the cavity has to be in tune with the laser wavelength. This is generally done by adjusting the position of one of the two mirrors. When the laser is in resonance with a cavity mode, intensity builds up in the cavity due to constructive interference. When the light entering the cavity is extinguished, the intensity of the light in the ring-down cavity, when empty, decays at a pre-determined rate. A small fraction of the light is not reflected by the mirrors and escapes the ring-down cavity. The intensity of the escaping light is measured by a sensor component to determine the decay rate.

When a sample is placed in the ring-down cavity, analytes (e.g., volatile organic compounds) present in the sample absorb some of the light, thereby accelerating the decay of the intensity of the light in the ring-down cavity. Absorption spectra are generated by measuring the decay times of the light in the presence of the sample at specific wavelengths relative to the decay times of the light in the absence of the sample at these wavelengths. Identification and quantification of individual analytes in the sample can be achieved via a number of methods, such as, for example, the performance of a linear regression of the measured absorption spectra for the sample with the known absorption spectra of various analytes.

While individual analytes can be readily identified, the particular analytes that can be used to positively detect the presence or absence of a particular physiological condition can be unclear, such as is the case for lung cancer. Breath samples can be collected from a patient in a non-invasive manner and analyzed via CRDS, but, as there is no widely accepted agreement on the analytes that evidence the presence or absence of lung cancer in breath, and as the breath samples contain numerous confounding components that can make detection of single analytes difficult, a different approach is required.

SUMMARY OF THE DISCLOSURE

In one aspect, there is provided a method for analyzing a sample using cavity ring-down spectroscopy, comprising:

loading at least part of a sample in a ring-down cavity; for each of a set of wavelengths: generating, via at least one laser, a laser beam at the wavelength directed into the ring-down cavity; extinguishing the laser beam entering the ring-down cavity; and registering light intensity decay data for light exiting the ring-down cavity via a light intensity sensor system; and determining, via at least one processor, a probability from the light intensity decay data for the set of wavelengths that a subject from which the sample was received has a physiological condition or a degree of a physiological condition at least indirectly using a dataset of light intensity decay data for previously analyzed samples for which the presence or absence of the physiological condition or the degree of the physiological condition has been identified.

The determining can include using a predictive model that is at least partially based on the dataset of light intensity decay data.

The physiological condition can be lung cancer.

The sample and previously analyzed samples can be breath samples.

The set of wavelengths can be a first set of wavelengths, the sample can be loaded from a thermal desorption tube, the at least part of the sample can be a first part of the sample that is desorbed from the thermal desorption tube heated to a first desorption temperature to load the at least first part of the sample into the ring-down cavity, and the method can further comprise: loading a second part of the sample desorbed from the thermal desorption tube heated to a second desorption temperature; for each of a second set of wavelengths: generating, via at least one laser, a laser beam at the wavelength directed into the ring-down cavity; extinguishing the laser beam entering the ring-down cavity; and registering light intensity decay data for light exiting the ring-down cavity via a light intensity sensor system.

The second set of wavelengths can be equal to the first set of wavelengths.

The method can further include combining the light intensity decay data from the second part of the sample to the light intensity decay data from the first part of the sample for each of the first set of wavelengths.

The determining can be performed using a predictive model trained at least partially using the dataset of light intensity decay data for previously analyzed samples.

The generating, the extinguishing, and the registering can be performed until a control module determines that a desired level of light intensity decay data has been collected.

In another aspect, there is provided a system for analyzing a sample using cavity ring-down spectroscopy, comprising: a ring-down cavity; at least one laser operable to generate a laser beam at each of a set of wavelengths, the laser beam being directed into the ring-down cavity; a sample-loading system for loading at least part of a sample into the ring-down cavity for analysis, and for unloading the at least part of the sample from the ring-down cavity; a light intensity sensor system positioned to register light intensity decay data for light exiting the ring-down cavity; at least one processor operably coupled to the sample-loading system, the at least one laser, and the light intensity sensor system; a storage storing computer-readable instructions that, when executed by the at least one processor, cause the at least one processor to: control the sample-loading system to load the at least part of the sample into the ring-down cavity; for each of the set of wavelengths: operate the at least one laser to generate the laser beam directed into the ring-down cavity; extinguish the laser beam entering the ring-down cavity; and register light intensity decay data for light exiting the ring-down cavity via the light intensity sensor system; and determine a probability from the light intensity decay data for the set of wavelengths that a subject from which the sample was received has a physiological condition or a degree of a physiological condition at least indirectly using a dataset of light intensity decay data for previously analyzed samples for which the presence or absence of the physiological condition or the degree of the physiological condition has been identified.

The at least one processor can determine the probability using a predictive model that is at least partially based on the dataset of light intensity decay data.

The physiological condition can be lung cancer.

The sample and previously analyzed samples can be breath samples.

The set of wavelengths can be a first set of wavelengths, the sample can be provided in a thermal desorption tube, the at least part of the sample can be a first part of the sample, the at least one processor can control the sample loading system to desorb the first part of the sample by heating the thermal desorption tube to a first desorption temperature to load the first part of the sample into the ring-down cavity, and the at least one processor can control the sample-loading system to desorb a second part of the sample by heating the thermal desorption tube to a second desorption temperature to load the second part of the sample into the ring-down cavity after unloading the first part of the sample from the ring-down cavity, and the at least one processor, for each of a second set of wavelengths can: operate the at least one laser to generate the laser beam directed into the ring-down cavity; extinguish the laser beam entering the ring-down cavity; and register light intensity decay data for light exiting the ring-down cavity via the light intensity sensor system.

The second set of wavelengths can be equal to the first set of wavelengths.

The at least one processor can combine the light intensity decay data from the second part of the sample to the light intensity decay data to the first part of the sample for each of the first set of wavelengths.

The at least one processor can determine the probability from the light intensity decay data using a predictive model trained at least partially using the dataset of light intensity decay data for previously analyzed samples.

The at least one processor can repeat the operating extinguishing, and registering until the at least one processor determines that a desired level of light intensity decay data has been collected.

In a further aspect, there is provided a method for analyzing a sample using cavity ring-down spectroscopy, comprising: heating a thermal desorption tube to a first desorption temperature to desorb a first part of a sample contained therein; loading the first part of the sample into a ring-down cavity; for each of a first set of wavelengths: generating, via at least one laser, a laser beam at the wavelength that is directed into the ring-down cavity; extinguishing the laser beam entering the cavity; and registering light intensity decay data for light exiting the ring-down cavity via a light intensity sensor system; unloading the first part of the sample from the ring-down cavity; heating the thermal desorption tube to a second desorption temperature to desorb a second part of the sample contained therein; loading the second part of the sample into the ring-down cavity; for each of a second set of wavelengths: generating, via the at least one laser, a laser beam at the wavelength that is directed into the ring-down cavity; extinguishing the laser beam entering the cavity; and registering light intensity decay data for light exiting the ring-down cavity via the light intensity sensor system; and analyzing the light intensity decay data desorbed at the first desorption temperature and the light intensity decay data desorbed at the second desorption temperature.

The first set of wavelengths can be equal to the second set of wavelengths.

The method can further include combining the light intensity decay data from the second part of the sample to the light intensity decay data from the first part of the sample for each of the first set of wavelengths.

The second desorption temperature can be greater than the first desorption temperature.

The first desorption temperature can be equal to the second desorption temperature.

The analyzing can include determining a probability from the light intensity decay data for the first part of the sample and the light intensity decay data for the second part of the sample that a subject from which the sample was received has a physiological condition or a degree of the physiological condition at least indirectly using a dataset of light intensity decay data for previously analyzed samples for which the presence or absence of the physiological condition or the degree of the physiological condition has been identified.

The determining can be performed using a predictive model trained at least partially using the dataset of light intensity decay data for previously analyzed samples.

In still another aspect, there is provided a system for analyzing a sample using cavity ring-down spectroscopy, comprising: a ring-down cavity; at least one laser operable to generate a laser beam directed into the ring-down cavity; a sample-loading system for loading an at least part of a sample into the ring-down cavity for analysis, and for unloading the at least part of the sample from the ring-down cavity, the sample loading system including a heater configured to heat a thermal desorption tube containing the sample; a light intensity sensor system positioned to register light intensity decay data for light exiting the ring-down cavity; at least one processor operably coupled to the sample-loading system, the at least one laser, and the light intensity sensor system; a storage storing computer-readable instructions that, when executed by the at least one processor, cause the at least one processor to: control the sample-loading system to heat the thermal desorption tube to a first desorption temperature to desorb a first part of the sample contained therein, and load the first part of the sample into the ring-down cavity; for each of a first set of wavelengths: operate the at least one laser to generate the laser beam directed into the ring-down cavity at the wavelength; extinguish the laser beam entering the ring-down cavity; and register light intensity decay data for light exiting the ring-down cavity via the light intensity sensor system; unload the first part of the sample from the ring-down cavity; control the sample-loading system to heat the thermal desorption tube to a second desorption temperature to desorb a second part of the sample contained therein, and load the second part of the sample into the ring-down cavity; for each of a second set of wavelengths: operate the at least one laser to generate the laser beam directed into the ring-down cavity at the wavelength; extinguish the laser beam entering the ring-down cavity; and register light intensity decay data for light exiting the ring-down cavity via the light intensity sensor system; and analyze the light intensity decay data desorbed at the first desorption temperature and the light intensity decay data desorbed at the second desorption temperature.

The first set of wavelengths can be equal to the second set of wavelengths.

The computer executable instructions, when executed by the at least one processor, can cause the at least one processor to combine the light intensity decay data from the second part of the sample to the light intensity decay data from the first part of the sample for each of the first set of wavelengths.

The second desorption temperature can be greater than the first desorption temperature.

The first desorption temperature can be equal to the second desorption temperature.

The computer executable instructions, when executed by the at least one processor, can cause the at least one processor to determine a probability from the light intensity decay data for the first part of the sample and the light intensity decay data for the second part of the sample that a subject from which the sample was received has a physiological condition or a degree of the physiological condition at least indirectly using a dataset of light intensity decay data for previously analyzed samples for which the presence or absence of the physiological condition or the degree of the physiological condition has been identified.

The determining can be performed using a predictive model trained at least partially using the dataset of light intensity decay data for previously analyzed samples.

In still yet another aspect, there is provided a method for generating a predictive model for cavity ring-down spectroscopy analysis, comprising: for each of a plurality of samples being identified as having a physiological condition or a degree of the physiological condition, each of the samples being stored in at least two thermal desorption tubes, and for each of at least two mutually unique sequences of desorption temperatures: selecting a previously unselected one of the at least two thermal desorption tubes containing the sample; for each desorption temperature in the sequence, in order: heating the previously unselected one of the at least two thermal desorption tubes to the desorption temperature to desorb a part of the sample contained therein; loading the part of the sample into a ring-down cavity; for each of a set of wavelengths: generating, via at least one laser, a laser beam at the wavelength that is directed into the ring-down cavity; extinguishing the laser beam entering the ring-down cavity; and registering light intensity decay data for the wavelength for the part of the sample; and unloading the part of the sample from the ring-down cavity; and identifying which of the at least two mutually unique sequences of desorption temperatures for which the light intensity decay data has a greater correlation with the presence or absence of the physiological condition or the degrees of the physiological condition with which the plurality of samples have been identified.

Each subsequent desorption temperature in at least one of the at least two sequences of desorption temperatures can be higher than a previous desorption temperature in the at least one of the at least two sequences of desorption temperatures.

In another aspect, there is provided a system for generating a predictive model for cavity ring-down spectroscopy analysis, comprising: a ring-down cavity; at least one laser operable to generate a laser beam directed into the ring-down cavity; a sample-loading system for loading an at least part of a sample into the ring-down cavity for analysis, and for unloading the at least part of the sample from the ring-down cavity, the sample loading system including a heater configured to heat a thermal desorption tube containing the sample; a light intensity sensor system positioned to register light intensity decay data for light exiting the ring-down cavity; at least one processor operably coupled to the sample-loading system, the at least one laser, and the light intensity sensor system; a storage storing computer-readable instructions that, when executed by the at least one processor, cause the at least one processor to: for each of a plurality of samples being identified as having a physiological condition or a degree of the physiological condition, each of the samples being stored in at least two thermal desorption tubes, and for each of at least two mutually unique sequences of desorption temperatures: select a previously unselected one of the at least two thermal desorption tubes containing the sample; for each desorption temperature in the sequence, in order: heat the previously unselected one of the at least two thermal desorption tubes to the desorption temperature to desorb a part of the sample contained therein; load the part of the sample into a ring-down cavity; for each of a set of wavelengths: generate, via at least one laser, a laser beam at the wavelength that is directed into the ring-down cavity; extinguish the laser beam entering the ring-down cavity; and register light intensity decay data for the wavelength for the part of the sample; and unload the part of the sample from the ring-down cavity; and identify which of the at least two mutually unique sequences of desorption temperatures for which the light intensity decay data has a greater correlation with the presence or absence of the physiological condition or the degrees of the physiological condition with which the plurality of samples have been identified.

Each subsequent desorption temperature in at least one of the at least two sequences of desorption temperatures can be higher than a previous desorption temperature in the at least one of the at least two sequences of desorption temperatures.

In a further aspect, there is provided a method for analyzing a sample using cavity ring-down spectroscopy, comprising: heating a thermal desorption tube to a first desorption temperature to desorb a first part of a sample contained therein; expelling the first part of the sample without performing cavity ring-down spectroscopy thereon; heating the thermal desorption tube to a second desorption temperature that differs from the first desorption temperature to desorb a second part of the sample contained therein; loading the second part of the sample into the ring-down cavity; for each of a second set of wavelengths: generating, via the at least one laser, a laser beam at the wavelength that is directed into the ring-down cavity; extinguishing the laser beam entering the cavity; and registering light intensity decay data for light exiting the ring-down cavity via the light intensity sensor system; and analyzing the light intensity decay data.

The analyzing can include determining a probability from the light intensity decay data for the second part of the sample that a subject from which the sample was received has a physiological condition or a degree of the physiological condition at least indirectly using a dataset of light intensity decay data for previously analyzed samples for which the presence or absence of the physiological condition or the degree of the physiological condition has been identified.

In a further aspect, there is provided a system for analyzing a sample using cavity ring-down spectroscopy, comprising: a ring-down cavity; at least one laser operable to generate a laser beam directed into the ring-down cavity; a sample-loading system for loading an at least part of a sample into the ring-down cavity for analysis, and for unloading the at least part of the sample from the ring-down cavity, the sample loading system including a heater configured to heat a thermal desorption tube containing the sample; a light intensity sensor system positioned to register light intensity decay data for light exiting the ring-down cavity; at least one processor operably coupled to the sample-loading system, the at least one laser, and the light intensity sensor system; a storage storing computer-readable instructions that, when executed by the at least one processor, cause the at least one processor to: heat a thermal desorption tube to a first desorption temperature to desorb a first part of a sample contained therein; expel the first part of the sample without performing cavity ring-down spectroscopy thereon; heat the thermal desorption tube to a second desorption temperature that differs from the first desorption temperature to desorb a second part of the sample contained therein; load the second part of the sample into the ring-down cavity; and for each of a second set of wavelengths: generate, via the at least one laser, a laser beam at the wavelength that is directed into the ring-down cavity; extinguish the laser beam entering the cavity; and register light intensity decay data for light exiting the ring-down cavity via the light intensity sensor system; and analyze the light intensity decay data.

The computer executable instructions, when executed by the at least one processor, can cause the at least one processor to determine a probability from the light intensity decay data for the second part of the sample that a subject from which the sample was received has a physiological condition or a degree of the physiological condition at least indirectly using a dataset of light intensity decay data for previously analyzed samples for which the presence or absence of the physiological condition or the degree of the physiological condition has been identified.

Other technical advantages may become readily apparent to one of ordinary skill in the art after review of the following figures and description.

BRIEF DESCRIPTIONS OF THE DRAWINGS

For a better understanding of the embodiment(s) described herein and to show more clearly how the embodiment(s) may be carried into effect, reference will now be made, by way of example only, to the accompanying drawings in which.

Figure 1:
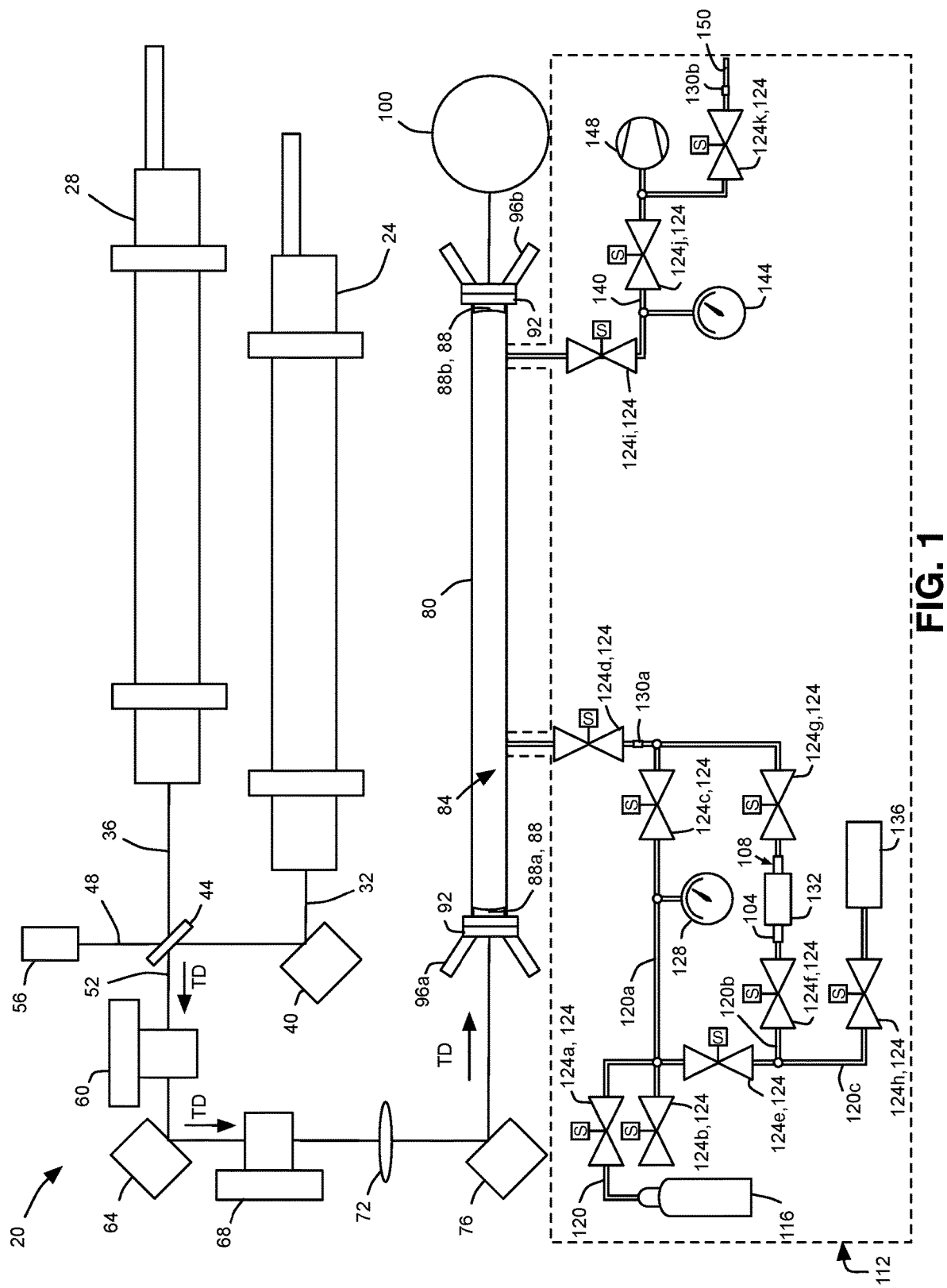
FIG. 1 is a schematic diagram of various optical and pneumatic components of a CRDS system in accordance with one embodiment.

Unless otherwise specifically noted, articles depicted in the drawings are not necessarily drawn to scale.

DETAILED DESCRIPTION

For simplicity and clarity of illustration, where considered appropriate, reference numerals may be repeated among the Figures to indicate corresponding or analogous elements. In addition, numerous specific details are set forth in order to provide a thorough understanding of the embodiment or embodiments described herein. However, it will be understood by those of ordinary skill in the art that the embodiments described herein may be practiced without these specific details. In other instances, well-known methods, procedures and components have not been described in detail so as not to obscure the embodiments described herein. It should be understood at the outset that, although exemplary embodiments are illustrated in the figures and described below, the principles of the present disclosure may be implemented using any number of techniques, whether currently known or not. The present disclosure should in no way be limited to the exemplary implementations and techniques illustrated in the drawings and described below.

Various terms used throughout the present description may be read and understood as follows, unless the context indicates otherwise: "or" as used throughout is inclusive, as though written "and/or"; singular articles and pronouns as used throughout include their plural forms, and vice versa; similarly, gendered pronouns include their counterpart pronouns so that pronouns should not be understood as limiting anything described herein to use, implementation, performance, etc. by a single gender; "exemplary" should be understood as "illustrative" or "exemplifying" and not necessarily as "preferred" over other embodiments. Further definitions for terms may be set out herein; these may apply to prior and subsequent instances of those terms, as will be understood from a reading of the present description.

Modifications, additions, or omissions may be made to the systems, apparatuses, and methods described herein without departing from the scope of the disclosure. For example, the components of the systems and apparatuses may be integrated or separated. Moreover, the operations of the systems and apparatuses disclosed herein may be performed by more, fewer, or other components and the methods described may include more, fewer, or other steps. Additionally, steps may be performed in any suitable order. As used in this document, "each" refers to each member of a set or each member of a subset of a set.

Any module, unit, component, server, computer, terminal, engine or device exemplified herein that executes instructions may include or otherwise have access to computer readable media such as storage media, computer storage media, or data storage devices (removable and/or non-removable) such as, for example, magnetic disks, optical disks, or tape. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by an application, module, or both. Any such computer storage media may be part of the device or accessible or connectable thereto. Further, unless the context clearly indicates otherwise, any processor or controller set out herein may be implemented as a singular processor or as a plurality of processors. The plurality of processors may be arrayed or distributed, and any processing function referred to herein may be carried out by one or by a plurality of processors, even though a single processor may be exemplified. Any method, application or module herein described may be implemented using computer readable/executable instructions that may be stored or otherwise held by such computer readable media and executed by the one or more processors.

The following disclosure presents a novel approach to performing analysis using CRDS. Unlike in traditional approaches in which light intensity decay data is compared to light intensity decay data for single known analytes, the light intensity decay data registered for a sample is analyzed at least indirectly using a dataset of light intensity decay data for a set of previously analyzed samples that have been identified as having a physiological condition or a degree of a physiological condition. In a preferred embodiment, this is done with a predictive model generated using machine learning on a set of training data. In addition, a process of incrementally desorbing the sample from the thermal desorption tube can be used to provide additional information about the sample. Still further, a predictive model can be improved by using machine learning to determine which combinations of desorption temperatures and/or wavelengths provide light intensity decay data that has a greater correlation with the physiological condition or the degrees of the physiological condition with which the plurality of samples have been identified.

A physiological condition is any type of state that a subject can be in. Physiological conditions can include diseases, infections, functional states of one or more organs or body systems, etc. Degrees of physiological conditions can include severities, stages (such as cancer stages), growth size, glandular output, etc. Degrees of a physiological condition can be binary in some scenarios to represent the presence or absence of the physiological condition in subjects. Degrees may be discrete or may be continuous.

Various components of a CRDS system 20 for analyzing a sample in accordance with a particular embodiment are shown in FIG. 1. A CO2 laser 24 and a carbon-13 O2 laser 28 are provided. The CO2 laser 24 and the carbon-13 O2 laser 28 are gas tube lasers that emit at a series of quasi-evenly-spaced, well-known frequencies that can be rapidly selected using an adjustable diffraction grating apparatus. Gas tube laser technology has a long history and is a stable and robust way of generating infrared radiation at precisely-known frequencies. Both the CO2 laser 24 and the carbon-13 O2 laser 28 emit light in the mid-IR spectrum.

Each of the CO2 laser 24 and the carbon-13 O2 laser 28 has an actuator and an output coupler that enable adjustment of the length of the laser cavity as well as an actuator to change the angle of grating at the back of the cavity, thereby changing its pitch to adjust which wavelengths it reflects. By both adjusting the length of the laser cavity and changing the angle of the grating, the laser can be very accurately tuned to a specific wavelength and desired mode quality.

The CO2 laser 24 produces a first laser beam 32, and the carbon-13 O2 laser 28 produces a second laser beam 36. Depending on the light frequency desired, either the CO2 laser 24 is tuned and generates the first laser beam 32 while the carbon-13 O2 laser 28 is detuned, or the carbon-13 O2 laser 28 is tuned and generates the second laser beam 36 while the CO2 laser 24 is detuned. In this manner, at most only one of the CO2 laser 24 and the carbon-13 O2 laser 28 outputs a beam at any particular time so that the first beam 32 and the second beam 36 are not combined simultaneously. Mid-infrared, and specifically long wavelength infrared, was chosen as the type of light as most volatile organic compounds absorb light in this range. As a result, multiple volatile organic compounds can be measured by a single system. CO2 lasers operate in this range and have sufficient power and linewidth narrowness for ring-down spectroscopy. Using two lasers adds to the range and number of available wavelengths that the CRDS system 20 can use to analyze samples.

The first laser beam 32 is redirected via a mirror 40 on an optic mount towards a beam splitter 44. The beam splitter 44 is partially reflective and partially transmissive, and splits each of the first laser beam 32 and the second laser beam 36 into two beams, a sampling beam 48, and a working beam 52 that has the same characteristics as the sampling beam 48 and can be of similar intensity as the sampling beam 48.

The sampling beam 48 is received by a fast infrared detector 56. The fast infrared detector 56 measures the amplitude and the beat frequency of the sampling beam 48 using an oscilloscope. The beat frequency can indicate the presence of higher order modes resulting from a less-than-optimal tuning of the CO2 laser 24 or the carbon-13 O2 laser 28. In response to the detection of an undesirable beat frequency, the corresponding laser 24 or 28 is tuned until the amplitude of the beat frequency is minimized or eliminated while maximizing the intensity. If the amplitude of the beat frequency cannot be reduced below an acceptable level, the laser can be tuned to a different wavelength.

The working beam 52 continues to a first optical modulator 60, which then deflects the working beam 52 to a mirror 64 on an optic mount. The mirror 64 redirects the light towards a second optical modulator 68 that, in turn, deflects the working beam 52 to a focusing lens 72. The optical modulators are used to control the intensity of the light beam generated by the laser. In the present embodiment, the first and second optical modulators 60, 68 are acousto-optic modulators ("AOMs"), also referred to as Bragg cells. AOMs are one type of optical modulator that uses a piezoelectric transducer coupled to a material such as germanium or glass. In the described embodiment, the material is germanium. When an oscillating electric signal is applied to the piezoelectric transducer, the piezoelectric transducer vibrates, creating sound waves in the material. These sound waves expand and compress the material, thereby creating periodic variations in the refractive index and allowing for Bragg diffraction. Light entering the AOM at the first order Bragg angle relative to the plane perpendicular to the axis of propagation of the acoustic wave will be deflected by an amount equal to twice the Bragg angle at maximum efficiency. Extinguishing the electric signal removes the Bragg diffraction properties of the material and causes the light to pass through undeflected, effectively attenuating the light along the deflected optical path. A by-product of the AOM is that the frequency of the light being deflected is shifted.

In other embodiments, the optical modulators could alternatively be electro-optic modulators. An electro-optic modulator is another type of optical modulator that applies a DC or low-frequency electric field to a material to distort the position, orientation, and/or shape of the molecules of the material. As a result, the refractive index is altered to change the phase of the outgoing beam as a function of the applied field. By sending the beam through a polarizer, the phase modulation is converted to intensity modulation. In another method, a phase modulator when placed in a branch of an interferometer can act as an intensity modulator.

Further, while the CRDS system 20 is described as having two optical modulators, in other embodiments, the CRDS system can have fewer or a greater number of optical modulators.

The first and second optical modulators 60, 68 act as attenuators to adjust the intensity of the working beam 52 and extinguish the beam at the commencement of a ring-down event. A ring-down event includes the extinguishing of the working beam 52 illuminating a ring-down cavity or the detuning of the laser for the ring-down chamber, and the collection of light intensity data from the ring-down chamber. As they are AOMs, the first and second optical modulators 60, 68 use the acousto-optic effect to diffract the light using sound waves (normally at radio-frequency). In each of the first and second optical modulators, a piezoelectric transducer is coupled to a material such as germanium or glass, and an oscillating electric signal is used to cause the piezoelectric transducer to vibrate. The vibrating piezoelectric transducer creates sound waves in the material that expand and compress the material, thereby creating period variations in the refractive index and allowing for Bragg diffraction. Light entering the AOM at Bragg angle relative to the plane perpendicular to the axis of propagation of the acoustic wave will be deflected by an amount equal to twice the Bragg angle at maximum efficiency. Extinguishing the electric signal removes the Bragg diffraction properties of the material and causes the light to pass through undeflected, effectively extinguishing the light along the deflected optical path. Hence, the intensity of the sound can be used to modulate the intensity of the light in the deflected beam.

The intensity of the light deflected by each of the first and second optical modulators 60, 68 can be between about 85%, representing a maximum deflection efficiency of the optical modulators 60, 68, and an attenuation limit of each of the first and second optical modulators 60, 68 of about 0.1% of the input light intensity. When the acoustic wave applied to the germanium is turned off, the deflected beam loses about 30 dB, or 99.9%, of the previous intensity. The attenuation limit means the upper limit of how much of the input light intensity can be reduced by the optical modulator.

Optic modulators are asymmetrical in that, as a side effect, they Doppler-shift the frequency of light in a first mode when the input light is received at a first end thereof, and they Doppler-shift the frequency of light in a second mode that is counter to the first mode when the input light is received at a second end thereof and the attenuation power is the same. The Doppler shift of the frequency of the light is, however, in the same direction regardless of whether the light enters at a first end or at a second end.

Conventional CRDS systems use a single optical modulator and, as a result, have a working beam that is frequency shifted. These frequency shifts are generally small in relation to the frequency of the light, and can change the manner in which the light is absorbed by matter in the cavity, but this frequency shift can be compensated for during the analysis. If diffraction is towards the acoustic wave source of an AOM, the frequency shift is downwards, and if diffraction is away from the acoustic wave source, the frequency shift is upwards. As discussed, the effect is minimal.

The working beam 52 deflected by the second optical modulator 68 is focused via a focusing lens 72. As the laser beam, and thus the working beam 52, travels from the CO2 laser 24 or the carbon-13 O2 laser 28, it continues to diverge. The focusing lens 72 focuses the working beam 52 back down.

A mirror 76 on an optic mount thereafter redirects the working beam 52 towards a ring-down chamber 80. The two mirrors 64, 76 extend the length of the path of the working beam 52.

The ring-down chamber 80 is an elongated tube defining a resonant cavity referred to as a ring-down cavity 84 therein. A front cavity mirror 88a and a rear cavity mirror 88b (alternatively referred to herein as cavity mirrors 88) are positioned at longitudinal ends of the ring-down cavity 84. The cavity mirrors 88 are highly reflective, both to light directed to the cavity mirrors 88 from outside of the ring-down cavity 84 and directed to the cavity mirrors 88 within the ring-down cavity 84. As a result, a fraction of the working beam 52 is directed at the front cavity mirror 88a, about 0.1%, passes through the front cavity mirror 88a, and enters the ring-down cavity 84, and the majority of the working beam 52, about 99.9% is reflected back towards the mirror 76.

The cavity mirrors 88 are mounted on mirror mounts 92 that are actuatable to adjust the positioning and orientation of the cavity mirrors 88. In particular, the front cavity mirror 88a towards the front of the ring-down cavity 84 is mounted on a mirror mount 92 that is actuatable via three mechanized micrometers 96a. The rear cavity mirror 88b towards the rear of the ring-down cavity 84 is mounted on a mirror mount 92 that is actuatable via three piezoelectric micrometers 96b that can be manually adjusted for optical alignment or with a piezo that allows them to be adjusted further with the piezo driver.

The angle of each of cavity mirror 88 can be changed so that they are sufficiently aligned so that when a light beam enters the ring-down cavity 84, the light beam does not deviate. If one of the cavity mirrors 88 is askew, then some of the light gets reflected to the side of the ring-down cavity 84, intensity of the light is lost, high-order modes result, amongst other things. The micrometers 96 can also be simultaneously tuned to change the length of the ring-down cavity 84 without affecting the angle alignment. This allows for the tuning of the ring-down cavity 84 so that the ring-down cavity 84 resonates at the frequency of the light that is entering the ring-down cavity 84.

The focusing lens 72 focuses the laser light to match the optical mode of the ring-down cavity 84, so that the minimum waist of the beam is positioned at the same place as the minimum beam waist of the ring-down cavity 84. The position of the focusing lens 72 can be adjusted to match the optical mode of a range of laser wavelengths.

A light intensity sensor system in the form of a liquid nitrogen-cooled detector 100 is positioned behind the rear cavity mirror 88b to receive light escaping through it. The liquid nitrogen-cooled detector 100 measures the intensity of the light that escapes the ring-down cavity 84. Other types of light intensity sensor systems for measuring the intensity of the escaping light can be used in place of the liquid nitrogen-cooled detector 100.

Samples are loaded into the ring-down cavity 84 from a thermal desorption tube 104 that is used to collect the samples for testing.

Figure 2:
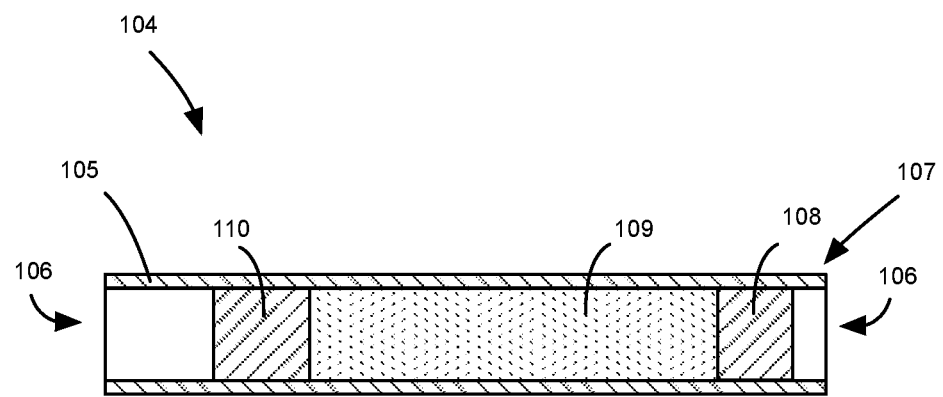
FIG. 2 is a sectional view of a thermal desorption tube used to load a breath sample into the ring-down cavity of the CRDS of FIGS. 1 and 2.

Referring now to FIG. 2, an exemplary thermal desorption tube 104 is shown. The thermal desorption tube 104 has a stainless-steel casing 105 that is tubular, defining an aperture 106 at each end thereof. A receiving end 107 of the thermal desorption tube 104 receives a sample. In the exemplary described embodiment, the sample is human breath collected from a human for testing. A foam separator 108 is positioned towards the receiving end and is configured to distribute fluid pressure more evenly across the cross-section of the stainless-steel casing 105. An adsorbent material 109 is positioned adjacent to the foam separator 108 and another foam separator 110. The separators may alternatively be made of a wire mesh or other suitable material. The adsorbent material 109 is very porous, has a relatively high surface area, and is selected for sampling specific compounds to trap and retain the compounds of interest even in the presence of other compounds. Further, the adsorbent material 109 allows the collected compounds to be easily desorbed or extracted for analysis. In addition, the solid adsorbent which is selected does not react with the sample. In the particular example, the solid adsorbent is Tenax or a carbon material. As a sample is received via the receiving end 107, the sample is more concentrated towards the receiving end 107 of the thermal desorption tube 104. In other embodiments, the composition and configuration of the thermal desorption tubes can vary, as will be appreciated by a person skilled in the art.

During sample collection, breath is collected via a breath collection apparatus into which the thermal desorption tube 104 is fit. The breath collection apparatus can be relatively small, such as a wearable mask, or can be relatively large, such as a tabletop unit into which a person breathes. The breath sample is received via the receiving end 107 of the thermal desorption tube 104. Human breath contains a variety of small and large molecules that are then trapped by the adsorbent material 109 in the thermal desorption tube 104. In other embodiments, other types of gaseous samples can be collected via the thermal desorption tubes.

Referring again to FIG. 1, a sample-loading system 112 is used to load samples from thermal desorption tubes 104 into the ring-down cavity 84, and evacuate the sample-loading system 112, including the ring-down cavity 84. During loading of a sample, the sample-loading system 112 fills the ring-down cavity 84 with at least part of the sample that has been collected (i.e., to desorb the sample from the thermal desorption tube 104, get the sample into the ring-down cavity 84 without introducing contaminants), brings the pressure and temperature in the ring-down cavity to one atmosphere and 50 degrees Celsius, and seals the ring-down cavity 84. In this embodiment, the absorption spectra for a set of samples to which the measured absorption spectra are at least indirectly compared are determined at this pressure and temperature to ensure consistency between these parameters which can affect the results. In other embodiments, however, the pressure and temperature can be fixed at other levels for the known and measured absorption spectra. During evacuation of the at least part of a sample, the sample-loading system 112 cleans the previously provided sample from the ring-down cavity 84 and the various conduits for guiding samples from the thermal desorption tube 104 to the ring-down cavity 84.

The sample-loading system 112 has an intake portion that includes a nitrogen gas source 116. The nitrogen gas source 116 is a supply of very clean nitrogen gas that is pressurized or that can pressurize the nitrogen gas to at least above one atmosphere of pressure. In the present embodiment, the nitrogen gas source 116 is pressurized at five psi above ambient pressure, but can be varied as long as the compression is sufficient to pressurize the ring-down cavity 84 to one atmosphere, or some other selected atmospheric pressure at which the analyses are run. In the illustrated embodiment, the nitrogen gas source 116 is the nitrogen gas that evaporates off a liquid nitrogen reservoir. The nitrogen gas source 116 is connected via conduit 120 to a gas inlet valve 124a. An auxiliary gas inlet valve 124b enables connection of other gases, but is not regularly employed. The gas inlet and auxiliary gas inlet valves 124a, 124b are in communication with a gas intake line 120a. A pressure meter 128 is positioned along the gas intake line 120a, as well as a gas intake line valve 124c. A filter 130a is positioned along the gas intake line 120a in front of a cavity inlet valve 124d that seals the gas intake line 120a from the ring-down cavity 84. The filter 130a inhibits the entry of contaminants into the ring-down cavity 84 where they can deposit on the cavity mirrors 88 and interfere with reflection.

The gas inlet and auxiliary gas inlet valves 124a, 124b are in communication with a pathing valve 124e. The pathing valve 124e enables or disables direct access to a desorption tube line 120b and a sample outlet line 120c.

The desorption tube line 120b includes a forward valve 124f and a rearward valve 124g. The thermal desorption tube 104 is positioned between the forward valve 124f and the rearward valve 124g, with the receiving end 107 of the thermal desorption tube 104 being positioned towards the rearward valve 124g. The thermal desorption tube 104 is positioned within a heater 132 that is controllable to heat the thermal desorption tube 104 to a range of temperatures.

The sample outlet line 120c includes a sample outlet valve 124h and a mass flow controller 136.

The sample-loading system 112 also has an outlet portion that includes a cavity outlet valve 124i in communication with the ring-down cavity 84. An outlet line 140 is in communication with the cavity outlet valve 124i. A pressure meter 144 is positioned along the outlet line 140. A vacuum cutoff valve 124j is positioned between the pressure meter 144 and a vacuum pump 148. A vacuum intake valve 124k is in communication with the vacuum pump 148 and draws air through a pump intake line 150. A filter 130b is positioned in the pump intake line 150 to inhibit entry of contaminants that can interfere with the working of the vacuum pump 148.

Valves 124a to 124k may be alternatively referred to herein as valves 124.

While the cavity inlet valve 124d and the cavity outlet valve 124i are shown for convenience coupled to the ring-down cavity 84 at certain locations, it will be understood that the locations at which the valves 124d, 124i are coupled to the ring-down cavity 84 may vary. In a preferred configuration, the cavity inlet valve 124d is in communication with the ring-down cavity 84 towards an end thereof adjacent the front cavity mirror 88a and the cavity outlet valve 124i is in communication with the ring-down cavity 84 towards an end thereof adjacent the rear cavity mirror 88b.

When a new sample is to be loaded into the ring-down cavity 84, the thermal desorption tube 104 containing the new sample is coupled to the sample-loading system 112 as shown in FIG. 1.

During an evacuation phase, the vacuum intake valve 124k is opened and the vacuum pump 148 is turned on. The vacuum intake valve 124k is then closed, and the vacuum cutoff valve 124j, the cavity outlet valve 124i, the cavity inlet valve 124d, the gas intake line valve 124c, and the pathing valve 124e are opened in succession. The contents of the lines along this path and the ring-down cavity 84 are evacuated from the CRDS system 20 by the vacuum pump 148. The pressure meter 144 enables the determination of when the system has been evacuated sufficiently, especially when the pressure meter 128 is cut off from the vacuum pump 148. When it is determined that the system has been evacuated sufficiently, these same open valves 124j, 124i, 124d, 124c, and 124e are then closed in the reverse order. Thereafter, during a nitrogen fill phase, valves 124a, 124c, 124d, 124i, and 124j are opened to allow nitrogen gas from the nitrogen gas source 116 to fill the lines 120a and 140. The nitrogen gas is then purged using another evacuation phase. The nitrogen fill phase and the evacuation phase can be repeated as desired to clear out the lines. The CRDS system 20 is thus evacuated of the previously tested sample.

During the loading of the new sample, the thermal desorption tube 104 is flushed to remove carbon dioxide and water from the thermal desorption tube 104 so that the amount of carbon dioxide and water loaded into the ring-down cavity 84 is minimized. In order to flush the thermal desorption tube 104, the gas intake valve 124a, the gas intake line valve 124c, and the rearward valve 124g are opened to give a path to the nitrogen gas to forward flush the thermal desorption tube 104. The thermal desorption tube 104 is selected to inhibit the collection of carbon dioxide and water with the sample, but there is still typically some carbon dioxide and water in the thermal desorption tube 104.

500 ml of nitrogen gas is put through the thermal desorption tube to get out carbon dioxide and water that have remained in the thermal desorption tube 104 from the original sample. Then the forward valve 124f and the sample outlet valve 124h are opened to provide a path to the mass flow controller 136. The mass flow controller 136 allows the nitrogen gas and borne carbon dioxide and water to be released at a specified flow rate. In the present configuration, this flow rate is 500 ml/min. All the valves 124 are then closed.

Once the carbon dioxide and the water have been removed from the thermal desorption tube 104, the sample-loading system 112 is evacuated again using the same process discussed above to remove the nitrogen gas just introduced in the sample-loading system 112 lines. The heater 132 surrounding the thermal desorption tube 104 then heats the thermal desorption tube 104 to the desired temperature to thermally desorb the at least part of the new sample within the thermal desorption tube 104. The gas inlet valve 124a, the pathing valve 124e, the forward valve 124f, the rearward valve 124g, and the cavity inlet valve 124d are then opened to provide a direct path for the nitrogen gas from the nitrogen gas source 116, through the thermal desorption tube 104 having desorbed compounds of interest, and to the ring-down cavity 84.

It is desired to achieve a pressure of one atmosphere within the ring-down cavity 84 as all of the reference data collected and analyzed is at this pressure level, thereby ensuring that the results are repeatable.

The gas inlet valve 124a is toggled open and closed by the system, then the system waits for the pressure reading at the pressure meter 128 to stabilize and reach one atmosphere. If, upon stabilization of the pressure meter 128, the pressure reading is still below one atmosphere, the gas inlet valve 124a is toggled again to repeat the process until the pressure reading is one atmosphere. When the pressure meter 128 shows that the pressure level in the ring-down cavity 84 is one atmosphere, the valves are all closed.

If it is desired to desorb at multiple temperatures, the vacuum pump 148 is turned on, the cavity outlet valve 124i and the vacuum cutoff valve 124j are opened to evacuate the ring-down cavity 84. Then the cavity outlet valve 124i is closed before the desorption process is repeated.

A full evacuation is generally not performed between multiple desorptions as there is still some of the sample between the rearward valve 124g and the cavity inlet valve 124d that would be otherwise lost.

By pressurizing a fixed volume ring-down cavity containing the sample to a desired pressure level in this manner, the surface area within the ring-down cavity to which compounds can adhere can be decreased in comparison to variable volume ring-down cavities that may be used to raise the pressure within the cavity to the desired level.

Further, the pressure meter 128 is upstream from the path of the sample from the thermal desorption tube 104 to the ring-down cavity 84, thereby preventing its contamination by the sample.

Figure 3:
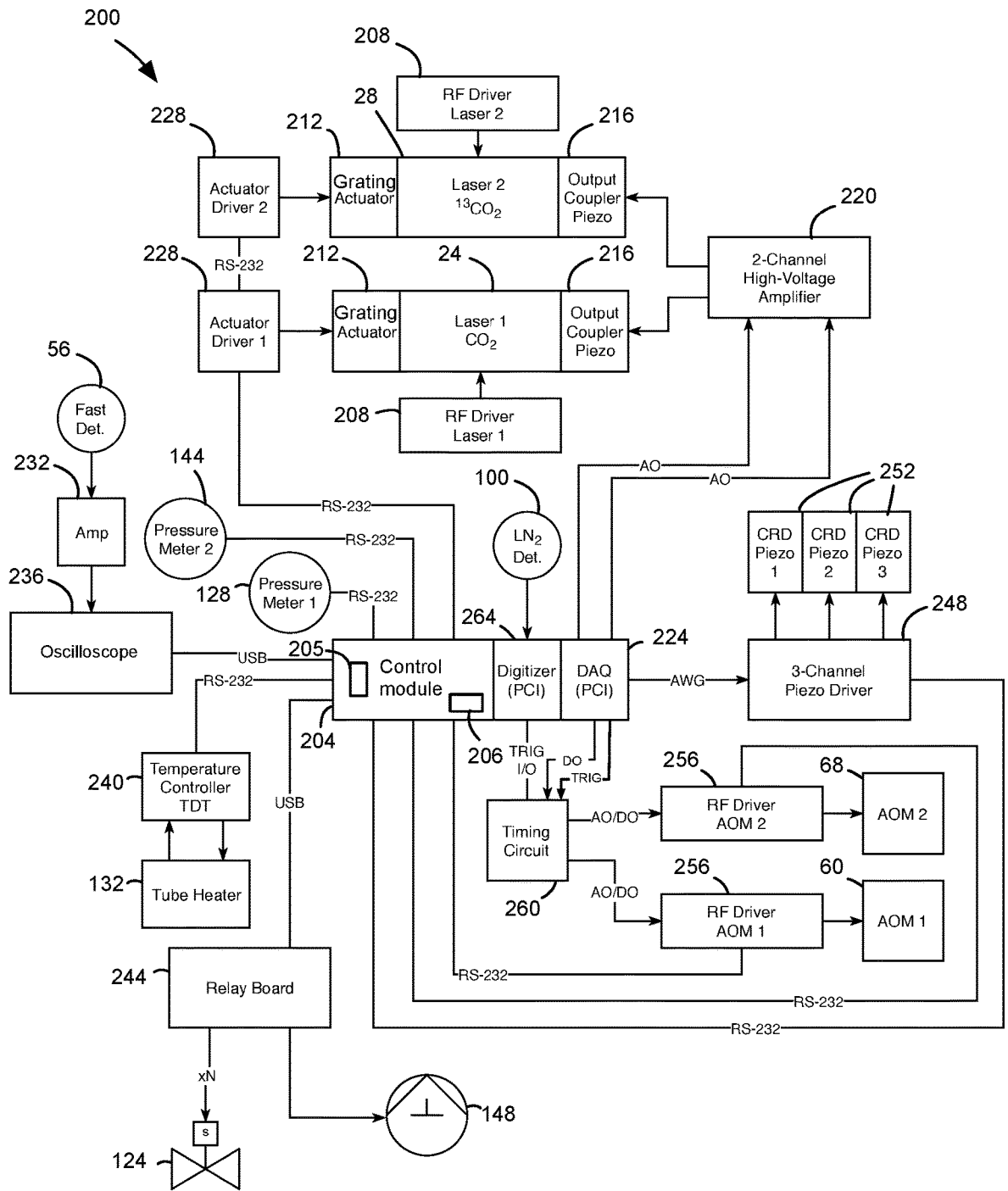
FIG. 3 is a schematic diagram of an electrical control system for controlling the various optical and pneumatic components of the CRDS system shown in FIG. 1.

FIG. 3 is a schematic diagram of an electronic control subsystem 200 for various components of the CRDS system 20 that are also illustrated. All of the lines represent electrical or electronic signals, with arrows representing unidirectional communications, setting of a voltage, etc., and lines that are not arrows representing bidirectional communications.

A control module 204 including one or more processors acts as a computer system that controls the function of the various components illustrated in FIG. 1. The control module 204 has one or more processors 205 and storage 206 storing computer-executable instructions that, when executed by the processor 205, cause the processor 205 to direct the other components of the CRDS system 20 as described herein. The control module 204 can be any type of component that includes at least one processor executing computer executable instructions to control operation of the other components of the CRDS system 20 as described herein.

A pair of RF drivers 208 send approximately 40 MHz signal to power the CO2 laser 24 and the carbon-13 O2 laser 28. Each of the lasers 24, 28 is tuned using an output coupler and a diffraction grating. A grating actuator 212 actuates (turns) the diffraction grating. Another actuator actuates (translates) the output coupler. Each output coupler is driven by a 1000V output coupler piezo 216. A two-channel high-voltage amplifier 220 that powers the output coupler piezos 216 is adjustable between 0V and 1000V. The high-voltage amplifier 220 is set with an analog output signal from a data acquisition ("DAQ") card 224 in the control module 204. The DAQ generates output between 0V and 10V, and the high-voltage amplifier 220 multiplies the signal by 100 to generate a signal of 0V to 1000V to power the output coupler piezo 216. Each grating actuator 212 that changes the angle for the grating is driven by an actuator driver 228 that is given instructions by the control module 204 via RS-232. Each grating actuator 212 is moved so many millimeters, which is translated into a pitch angle of the laser 24, 28.

Data signals from the pressure meters 128, 144 of the sample-loading system 112 are received through RS-232.

The fast infrared detector 56 is connected to a small amplifier 232 and an oscilloscope 236 that can be used to read the amplitude and frequency of the beat signal that is used to tune the lasers 24, 28.

A temperature controller 240 for the thermal desorption tube heater 132 is controlled via RS-232 by the control module 204. The tube heater 132 includes a temperature sensor and a piece of aluminum that has heating tape wrapped around it. The heating tape and the temperature sensor are both connected to the temperature controller 240 which is a PID (proportional integral derivative) controller. The PID controller sets and reads back the temperature via RS-232 to the main control module 204.

A relay board 244 is connected to the control module 204 and is used to turn on and off all of the solenoid valves 124 and the vacuum pump 148.

A three-channel piezo driver 248 drives piezo actuators 252 that actuate the micrometers 96b to adjust the length of the ring-down cavity 84. Each channel has two components: communications to the piezo driver through RS-232, and analog input from the DAQ card 224. In other embodiments, two or more piezo drivers can be employed.

Each optical modulator 60, 68 is driven with an RF driver 256 that sends approximately a 40 MHz signal. Changing the frequency of the RF driver 256 changes the Bragg angle for a given optical wavelength, or changes the optical wavelength that a given or fixed Bragg angle is attuned to. If the RF driver 256 is tuned to a specific frequency and set to full power, most of the working beam 52 (about 85%) gets through. If adjusted to 80%, 70%, then the optical modulator 60, 68 will attenuate. If the RF driver 256 is set to zero, the optical modulator 60, 68 shuts off completely. The frequency of the RF driver 256 is set through a component via RS232. An analog and digital component can set the amplitude and the on/off condition of the RF driver 256. In particular, the DAQ card 224 sends a signal via a digital output ("DO") to a timing circuit 260 which, in turn, generates the four necessary signals needed to enable and set the amplitude of the RF drivers. The timing circuit 260 is also in communication with the control module 204 via a digitizer 264, enabling the control module 204 to control its operation in either a steady state condition or a ring-down triggering condition in which the timing circuit 260 sets the four voltages to zero, and then returns to the previous voltage level after a pre-determined amount of time. The digitizer 264 sends a trigger pulse to the timing circuit 260 to cause the optical modulators 60, 68 to extinguish the laser light provided to the ring-down cavity 84 during a ring down event.

Figure 4:
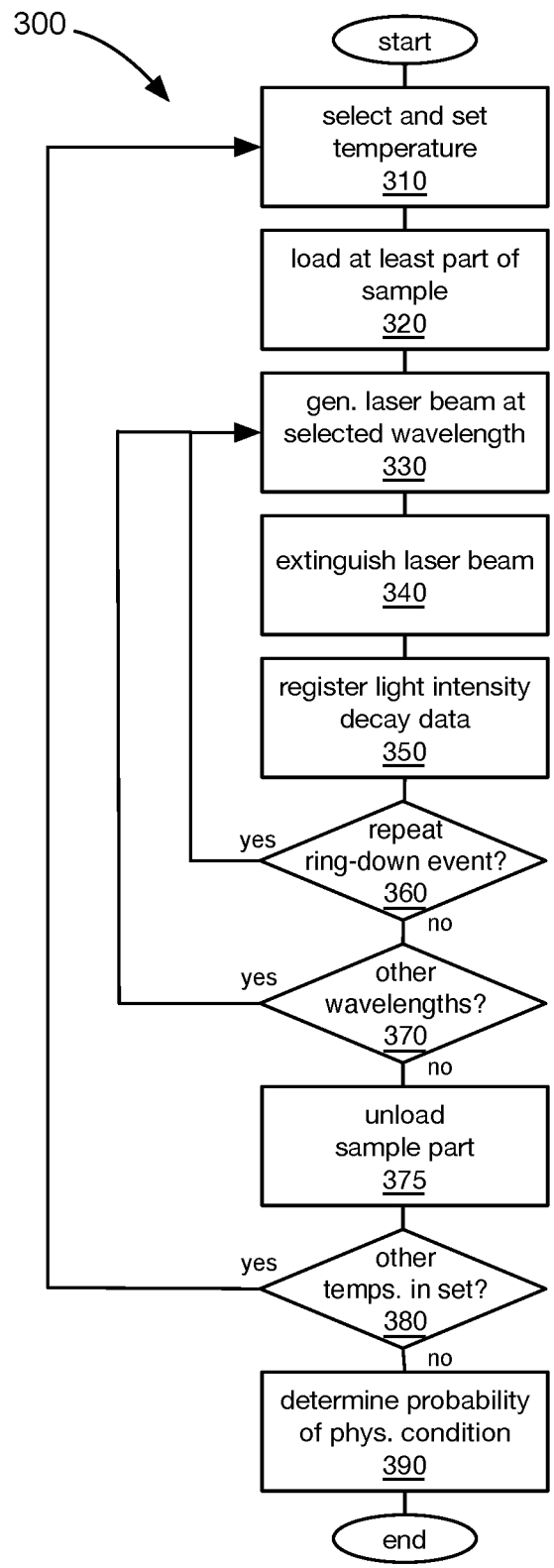
FIG. 4 shows the general method of analyzing a sample using the CRDS system of FIG. 1 in accordance with an embodiment.

A method 300 of analyzing a sample using the CRDS system 20 of FIG. 1 is shown in FIG. 4. Traditionally, the sample to be analyzed using CRDS is desorbed at a single temperature. In the method 300, a part of a sample in a thermal desorption tube is first desorbed at a first temperature, and then at least one additional part of the sample may be desorbed from the thermal desorption tube at at least one additional temperature. In some scenarios, it can be desirable to separate parts of the sample for analysis with the CRDS system 20. For example, acetone and ammonia can be desorbed from a thermal desorption tube at a lower temperature. As acetone and ammonia can overwhelm the spectra, obfuscating other substances in the sample, it can be desirable to desorb and analyze portions of the sample at different temperatures to isolate various substances from other substances. In other embodiments, it can be desirable to desorb the sample at the same temperature two or more times, as some constituents of the sample may desorb readily at that temperature the first time and other constituents of the sample may desorb less readily at that temperature the first time, but may desorb equally readily the second time. As the other constituents may have readily desorbed, they are less present to desorb the second time and thus the other constituents are more isolated. The set of ordered desorption temperatures thus can include a single desorption temperature or an ordered set of two or more desorption temperatures.

Referring now to FIGS. 1, 3, and 4, the method 300 begins with the setting of the temperature of the heater 132 to a first of the ordered set of desorption temperatures (310). In this particular configuration, a set of one or more temperatures at which the sample is to be desorbed from the thermal desorption tube 104 can be ordered. In one preferred approach, the desorption temperatures are ordered from lowest to highest. In another embodiment, the ordered set of desorption temperatures can include two desorption temperatures that are the same or similar. There can be benefit to desorbing a portion of a sample at a temperature to release readily desorbed components/compounds that is then analyzed, and then desorbing another portion of the sample at the same temperature to release less-readily desorbed components/compounds that can be analyzed with a reduced amount of the more readily desorbed components/compounds.

A first of the ordered set of desorption temperatures is selected, and the heater 132 is operated to heat the thermal desorption tube 104 to the first desorption temperature. Once the thermal desorption tube 104 is heated to the first desorption temperature via the heater 132, the part of the sample that has been desorbed at the first temperature is then loaded into the ring-down cavity 84, as previously described (320). Upon loading of the part of the sample in the ring-down cavity 84, a laser beam is generated by one of the lasers 24, 28 that is tuned to one of a set of wavelengths (330). The set of wavelengths can be selected from the wavelengths at which the lasers 24, 28 can produce a beam in any manner as desired. The generated laser beam is directed through the first optical modulator 60, reflected by the mirror 64, through the second optical modulator 68, and reflected by the mirror 72 into the ring-down chamber 80. The optical modulators 60, 68 attenuate the working beam 52 somewhat to modulate its intensity.

When the working beam 52 reaches the front cavity mirror 88a, a fraction, about 0.1%, penetrates the front cavity mirror 88a to enter the ring-down cavity 84. The majority of the working beam, about 99.9%, is initially reflected back along the same path to the working laser 24 or 28.

Initially, the ring-down cavity 84 is not illuminated. Light enters the ring-down cavity 84 and, as the majority of the light in the ring-down cavity 84 is reflected between the two cavity mirrors 88, the amount, or power, of light in the ring-down cavity 84 starts increasing as further light is introduced from outside via the working beam 52. A certain fraction of the light leaks out past the cavity mirrors 88. It takes a duration of time to "fill" the ring-down cavity 84 with light, and this can occur when the cavity length is equal to an adjacent resonance length of the ring-down cavity 84 for the tuned laser. At that point, there is an equilibrium between the incoming light and the leakage.

Once this equilibrium is achieved, the laser beam directed into the ring-down cavity 84 is extinguished (340). The laser beam entering the ring-down cavity 84 can be extinguished in a number of manners. In the particular embodiment, the digitizer 264 sends a trigger pulse to the timing circuit 260 to cause the optical modulators 60, 68 to extinguish the laser light provided to the ring-down cavity 84. In other embodiments, the laser can be turned off, or detuned so that it does not resonate for the configured cavity length, etc.

The timing circuit 260 simultaneously directs the first and second optical modulators 60, 68 to attenuate the light beam at or close to an attenuation limits of the optical modulators 60, 68 to reduce an intensity of the light beam from the first optical modulator 60. In the CRDS system 20, by directing both optical modulators 60, 68 to shut off simultaneously, the amount of light deflected by the first optical modulator 60 during the short span of time is markedly reduced by the second optical modulator 68 as it is shutting down.

The second optical modular 68 greatly increases the attenuation achieved via the first optical modulator 60 alone. In the currently described embodiment, if the first optical modulator 60 can attenuate by 30 dB, and the second optical modulator 68 can attenuate by an additional 30 dB, with the total attenuation achieved via the optical modulators 60, 68 being the sum of their attenuation, or 60 dB. During filling of the ring-down cavity 84 with light, the optical modulators 60, 68 attenuate the working beam 52 to modulate its intensity. In the present configuration, each of the optical modulators 60, 68 attenuate the working beam 52 by 5 dB, for a total attenuation of 10 dB. As a result, each of the optical modulators 60, 68 can still further attenuate the working beam 52 by 25 dB for a total further attenuation of 50 dB during the extinguishing of the working beam 52. In a conventional setup, one optical modulator would have to attenuate a working beam by 10 dB, leaving 20 dB of further attenuation available for extinguishing the working beam. As will be understood, the working beam 52 can be extinguished much more rapidly via 50 dB of further attenuation via the two optical modulators 60, 68 than with one optical modulator with 20 dB of further attenuation. As a result, the amount of additional light introduced into the ring-down cavity 84 after the optical modulators 60, 68 have been directed to shut down is a small fraction of the light further introduced by a single optical modulator setup in a conventional CRDS system. By extinguishing the working beam 52 more quickly, the measured decay of light in the ring-down cavity 84 is less affected by the additional light during the ramp-down times of the optical modulators 60, 68, thus granting higher precision when matching the observed decay times against known decay times.

Extinguishing of the laser light provided to the ring-down cavity 84 commences a ring-down event. The resonating laser light provided to the ring-down cavity 84 can be extinguished in other manners in alternative embodiments, such as, for example, by detuning the laser. By initiating the triggering of a ring-down event via a threshold, the ring-down event can be timed to occur during the peak while the ring-down cavity 84 is in resonance with the laser light, and not on one side of the peak. Further, as the bandwidth of the resonance is about 10 millivolts, the resolution of the piezo driver 248 is insufficiently granular to properly track the peak.

During the ring-down event, the control module 204 registers light intensity decay data reported by the liquid nitrogen-cooled detector 100 exiting from the back end of the ring-down cavity 84 (350). The ring-down event lasts about ten microseconds in the present configuration, but can last a longer or shorter time in other embodiments. The light decay time is about two microseconds.

It is then determined if the ring-down event is to be repeated (360). In this embodiment, the CRDS system 20 is configured to collected light intensity decay data for 500 ring-down events.

About 100 microseconds after when the ring-down event is triggered, the timing circuit 260 directs the optical modulators 60, 68 to recommence allowing the working beam 52 through to the ring-down cavity 84. If the light intensity decay data from 500 ring-down events has been captured, the control module 204 stops operation of the piezo driver 248, and then determines the decay rate from the ring-down event data, which refers to the light intensity decay data and may be used interchangeably herein. If, instead, it is determined at 360 that further light intensity decay data is to be collected, the control module 204 continues to direct the piezo driver 248 to actuate the rear cavity mirror 88b. As the aggregate voltage attains a maximum or minimum, it commences to proceed in an opposite direction. That is, if the aggregate voltage AV was increasing prior to achieving the maximum voltage in its range, the aggregate voltage AV then decreases back towards the voltage corresponding with the resonance length RL. Alternatively, if the aggregate voltage AV was decreasing prior to achieving the minimum voltage in its range, the aggregate voltage AV then increases back towards the voltage corresponding with the resonance length RL. In this manner, ring-down events are triggered in both directions.

The light intensity decay data is collected as quickly as possible, as various outputs can drift. For example, the piezo actuators 252 can have a settling time referred to as piezo creep.

In other embodiments, any number of ring-down events can be employed at each wavelength and desorption temperature. In one embodiment, the ring-down events at a wavelength and desorption temperature can be performed until a desired level of light intensity decay data has been collected. The light intensity decay data collected thus far can be quickly analyzed as it is collected to determine if it appears to be valid. After a desired number of ring-down events for which valid light intensity decay data is collected, the system can deem that sufficient data has been collected at that wavelength and desorption temperature. This can in many scenarios shorten the time required to perform the analysis.

Upon collecting the light intensity decay data for the selected wavelength, the light intensity decay data for the particular sample, desorption temperature, and wavelength may be processed by the control module 204, such as by determining a decay rate for each ring-down event and averaging these values. Other approaches can be employed to process the ring-down event data.

It is then determined if there are other wavelengths in the set at which the laser is to be generated (370). If there are other wavelengths to be generated, the method 300 returns to 330, at which the laser 24, 28 is tuned to generate a laser beam of the newly selected wavelength.

The process is repeated for lights of other wavelengths to generate an absorption spectrum for the sample at the particular desorption temperature. The light intensity data from the liquid nitrogen-cooled detector 100 provides or is readily converted to, in effect, light intensity decay data that indicates how quickly the light of the particular wavelength was absorbed by the part of the sample that was loaded into the ring-down cavity 84.

For example, the light generated by the CO2 laser 24 provides absorption coefficients for a range of wavelengths. Similarly, absorption coefficients can be generated for a range of wavelengths for the light from the carbon-13 O2 laser 28. In this manner, an absorption spectrum can be developed for the sample.

Once an absorption spectrum across the set of wavelengths is generated for the part of the sample desorbed at the first temperature, the part of the sample is unloaded from the ring-down cavity (375). It is determined if there are other temperatures in the ordered set to which the thermal desorption tube 104 is to be heated to desorb other parts of the sample for analysis in the ring-down cavity 84 (380). If it is determined that there are other temperatures at which a part of the sample is to be desorbed, the heater is set to the next desorption temperature at 310. In the present embodiment, a next desorption temperature to which the thermal desorption tube 104 is heated is higher than the previous desorption temperatures(s) to which the thermal desorption tube 104 was heated. If the ordered set of desorption temperatures includes a single desorption temperature, the method 300 does not return to 310.

As previously noted, desorption of the sample contained in the thermal desorption tube 104 at another temperature that is higher than other temperatures at which the thermal desorption tube 104 was previously desorbed can yield a different subset of the compounds/substance in the sample.

Once the light intensity decay data has been collected for each of the desorption temperatures, the CRDS system 20 analyzes the light intensity decay data for the set of wavelengths and the set of desorption temperatures to determine a probability that the patient from which the sample was drawn has a particular physiological condition or a degree of a physiological condition (390). The probability is determined at least indirectly using a dataset of light intensity decay data for previously analyzed samples for which the presence or absence of the physiological condition or a degree of the physiological condition (i.e., lung cancer in the exemplary embodiment) has been identified. The determination of the probability can use a predictive model that is at least partially based on the dataset of light intensity decay data for previously analyzed samples.

The CRDS system 20 can determine the probability that the subject from which the analyzed sample was drawn has one of a set of discrete degrees of the physiological condition, and then present the most likely degree of the physiological condition or the entire set of probabilities. Further, the CRDS system 20 can also provide a confidence level for each of the results.

The light intensity decay data collected at each desorption temperature can be analyzed at least indirectly using the dataset of light intensity decay data for the previously analyzed samples that is segregated by the same or similar desorption temperatures. Preferably, the dataset of light intensity decay data for the previously analyzed samples was collected using the same or a similar sequence of temperatures for desorbing parts of the sample. In an alternative embodiment, the light intensity decay data from two or more desorption temperatures from the sample can be combined together, and analyzed using a predictive model generated at least partially based on light intensity decay data for previously analyzed samples that is treated in the same or similar manner (i.e., the light intensity decay data for corresponding desorption temperatures is aggregated). A predictive model can be generated from the dataset of light intensity decay data for the previously analyzed samples. One preferred approach is by using supervised machine learning.

The dataset of light intensity decay data for previously analyzed samples represents spectra for entire parts of the previously collected samples and not any one particular volatile organic compound. By adopting this more holistic approach to analyzing a sample, there is less reliance on the identification of contentious volatile organic compounds to predict the probability that the sample currently being analyzed comes from a subject having the physiological condition. The subject can be a person or another animal or organism.

The predictive model is generated using machine learning techniques at least partially by using the dataset of light intensity decay data as a training set.

It can be challenging to obtain a sufficiently large sample dataset for predicting the presence or absence of certain physiological conditions. Some pre-processing steps can be beneficial in such circumstances. This can be particularly true for certain physiological conditions.

In order to manage missing values in the spectrum, interpolation techniques, such as spline interpolation, using neighboring absorbance values in the spectrum can be employed. If the available wavelengths are not evenly spaced, average values from comparable subjects identified by a k-nearest neighbor search can be used, as can a VOC regression approach to approximate missing values.

Where high variability is observed in the previously collected data, it can be attributable to natural VOC variations and other confounding variables. Baseline correction can be used to eliminate any unwanted trends, such as via the use of common spectroscopy detrending techniques (e.g., linear, quadratic, and Savitzky-Golay detrending). Spectral subtraction techniques can also be employed for highly concentrated VOCs like acetone and ammonia, which are common to all subjects and may be masking small, important details in the spectra.

Similarly, common normalization techniques can be used to improve sample consistency. In addition to those based on individual spectra (min-max, peak, standard normal variate normalization for example), methods that normalize across all spectra (such as multiplicative scatter correction) can be employed.

A comprehensive analysis of the spectra and clinical factors is used to identify unobvious relationships and confounders in the dataset of light intensity decay data for previously analyzed samples to improve data interpretation and identify subgroups that are incorporated into the predictive model. There are a number of confounding factors in breath VOC analysis that include age, sex, smoking, alcohol consumption, medication use, and other diseases. Unsupervised clustering techniques, along with supervised predictive models that classify spectra according to possible confounders, are used to assess these factors. Similarly, spectral data for different subgroups can be used to train separate models for lung cancer detection.

Features such as spectral derivative-based features, projected features, and wavelet transform-based features are being employed for feature extraction. Derivative-based features are particularly useful because they apply some inherent baseline and scale correction for inter-individual variability. Barcode features and a one-dimensional form of the local binary patterns (1D-LBP) can also be used. Further, features derived from a time-series of desorptions of samples at different temperature sequences can also be employed.

The various pre-processing and feature extraction methods can be combined, along with the information found in the confounding factor and subgroup analysis, to create the final classification system. To reduce system dimensionality and remove unhelpful, redundant features, a few feature selection techniques may be used. Statistics-based filter methods like minimum redundancy maximum relevance ("mRMR") selection can be employed, as well as classification-based wrapper methods, like sequential feature selection ("SFS") and genetic algorithm ("GA") selection. Simple support vector machine ("SVM"), discriminant analysis (LDA and QDA), and KNN classifiers can be employed to evaluate features in the wrapper selection methods and to build and validate the numerous classification models.

Various alternative approaches and methods can be employed for generating the predictive model.

Figure 5:
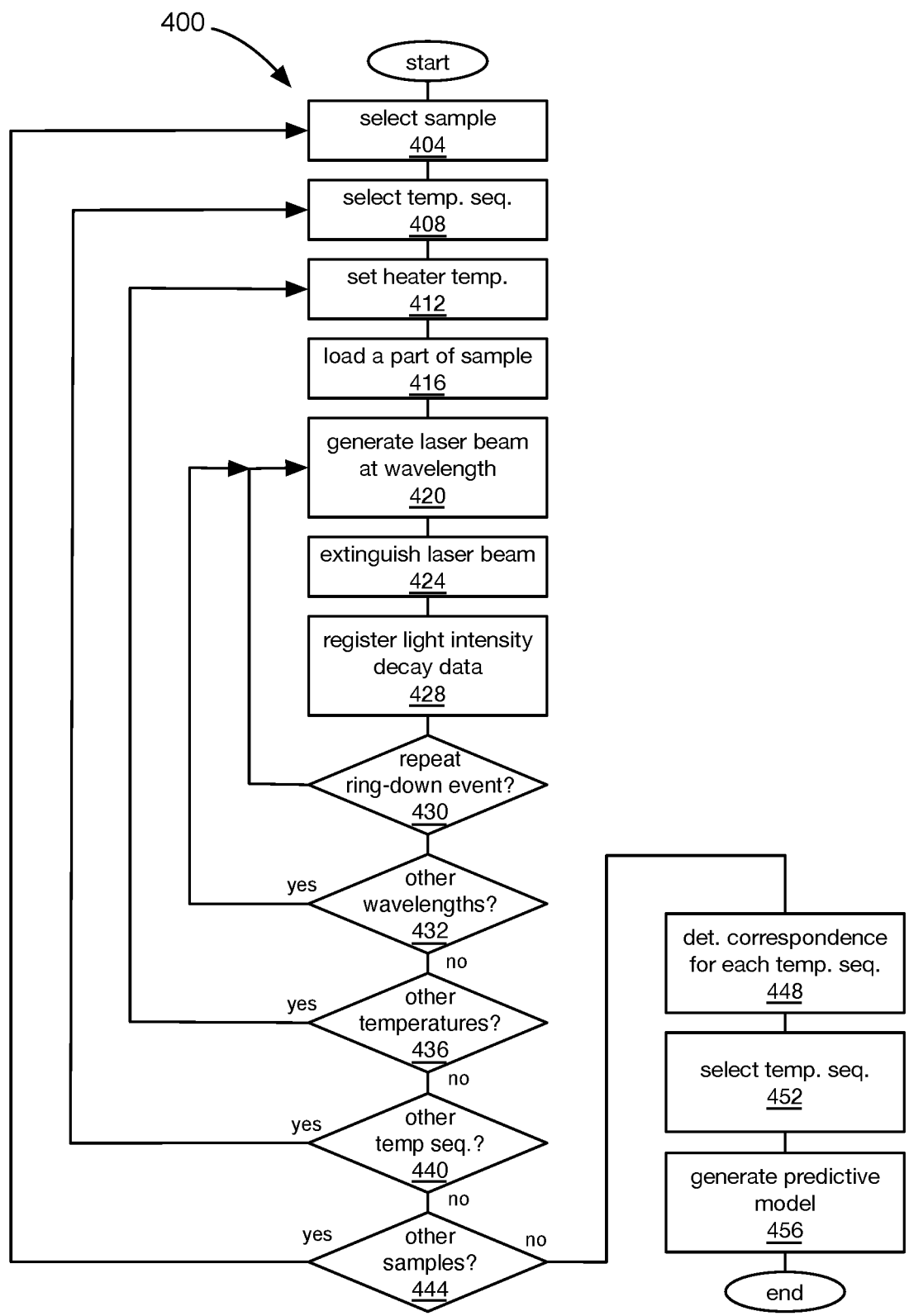
FIG. 5 shows a method of generating a predictive model using the CRDS system of FIG. 1 in accordance with an embodiment.

FIG. 5 shows a method 400 for generating a predictive model. In this approach, a set of desorption temperature sequences are identified for exploration. A sequence of desorption temperatures is an ordered set of temperatures to which the thermal description tube is heated to desorb parts of the sample contained therein. Desorption of the sample using a particular sequence of temperatures can enable different selective parts of the sample to be desorbed and analyzed separately, which can enable different aspects of the sample to be more readily identified. Certain features of a sample may be more readily apparent from the light intensity decay data captured for certain desorption temperature sequences. For example, if a first component/compound is desorbable from the thermal desorption tube 104 at a certain temperature and confounds a second component/compound that is desorbable at a slightly elevated temperature, features of the light intensity decay data for a sample may become more apparent using a desorption temperature sequence that has a desorption temperature equal to that of the first component/compound, and then a subsequent desorption temperature equal to or above that of the second component/compound. These relationships between the desorption temperature sequences and the features exposed may not in some cases be readily apparent. As a result, the particular sequence which yields the best correlation to the presence or absence may not be readily apparent without exploration. In another aspect, if the light intensity decay data registered at two desorption temperature sequences yield substantially equal correlations to the subset(s) of samples drawn from subjects having the physiological condition or a degree of the physiological condition, it may be desirable to select the shorter desorption temperature sequence, for example.

While the general method will be described with reference to the CRDS system 20, it will be understood that the approach may be conducted using a plurality of local or distributed CRDS systems and other computers using a common set of parameters and standard practices.

The method 400 commenced with the selection of sample (404). The sample is selected from a set of samples from subjects that have been identified as one of having a physiological condition and not having the physiological condition. Then a desorption temperature sequence is selected from a set of desorption temperature sequences (408). The set of desorption temperature sequences can be chosen based on scientific evidence, randomly, etc. The desorption temperature of the heater 132 is set to the next desorption temperature in the sequence (412). If the sequence is yet unprocessed, the first desorption temperature in the sequence is selected.

Next, a part of the sample is then desorbed and loaded (416). The heater 132 is heated to the selected desorption temperature from the sequence and a part of the sample is desorbed. the sample-loading system 112 loads the desorbed part of the sample into the ring-down cavity 84.

The control module 204 then operates one of the lasers 24, 28 to generate a laser beam of the selected wavelength. The laser beam is directed into the ring-down cavity 84 to "fill" the ring-down cavity 84 with light.

Once the control module 204 determines that there is sufficient light in the ring-down cavity 84, the control module 204 directs the optical modulators to extinguish the laser beam that is directed into the ring-down cavity 84 (424).

The liquid nitrogen-cooled detector 100 registers the light intensity exiting the ring-down cavity 84 via the rear cavity mirror 88*b* (428). Light intensity decay data corresponds to the detected intensity of the light exiting the ring-down cavity 84 over time, and is transmitted to the control module 204. Upon completion of the ring-down, the control module 204 determines whether to repeat the ring-down event (430). The ring-down event may be repeated many times to reduce the effect of abnormalities. If another ring-down event is to be performed at the selected wavelength, the method 400 returns to 420, wherein a laser beam at the selected wavelength is generated. It is then determined if there are other wavelengths in the set to be used (432). It there are other wavelengths, the method 400 returns to 420, at which a laser beam is generated at the next selected wavelength. If, instead, it is determined that there are no other wavelengths in the set, it is determined if there is another desorption temperature in the sequence (436). If there is at least another desorption temperature in the sequence, the next desorption temperature in the sequence is selected and the heater 132 is heated to that temperature to desorb another part of the sample at 412.

If, instead, it is determined that there are no other desorption temperatures in the sequence at 436, it is then determined whether there are other desorption temperature sequences to be explored (440). If there are other unexplored desorption temperature sequences, a next desorption temperature sequence is selected at 408. When a new desorption temperature sequence is selected, a new thermal desorption tube from the same subject is used, as the sample in the previously used thermal desorption tube 104 has been at least partially desorbed.

Once all of the desorption temperature sequences have been explored, it is determined if there are any other samples in the set that have yet to be analyzed (444). If there still yet unanalyzed samples in the set, another sample is selected at 404 for analysis.

If, instead, it is determined that all of the samples have been analyzed at 444, the correspondence between the light intensity decay data and the identification of the subjects from which the samples are drawn as having the physiological condition or degrees of the physiological condition for each desorption temperature sequence is then determined (448). The correspondence between the light intensity decay data and the identification of the samples as having the physiological condition or a degree of the physiological condition is stronger when there is a set of features that are significantly more prevalent in samples from subjects identified as having the physiological condition or a degree of the physiological condition. That is, if there is a particular set of features that each occurs in 85 percent of subjects having a physiological condition and in 20 percent of subjects not having the physiological condition for a particular sequence of desorption temperatures, then the light intensity decay data for the sequence of desorption temperatures may have a relatively good correlation to the presence or absence of the physiological condition in the subjects from which the samples are obtained. While this is an example, any pattern between the light intensity decay data and the presence of the physiological condition or a degree of the physiological condition can indicate the presence of a correlation between the light intensity decay data and the presence of the physiological condition or the degree of the physiological condition.

A desorption temperature sequence is then selected based on the correspondence between the light intensity decay data and the identification of the subject from which the samples were drawn as having the physiological condition or a degree of the physiological condition for each desorption temperature sequence (452). The desorption temperature sequence may be selected entirely based on the measured correlation, or on the correlation in combination with other factors. Other factors can determine the selection of the sequence of desorption temperatures, such as the number of desorption temperatures in the sequence, thereby determining the amount of time to perform the analysis.

A predictive model is then generated using the selected desorption temperature sequence at least partially selected based on the correlations (452).

Where a sequence of temperatures is used to desorb a sample from a thermal desorption tube, it can be unadvantageous to analyze parts of samples that are desorbed at certain temperatures. The desorption may be performed at certain temperatures to remove substances that are less of interest than those desorbed at other temperatures.

Figure 6:
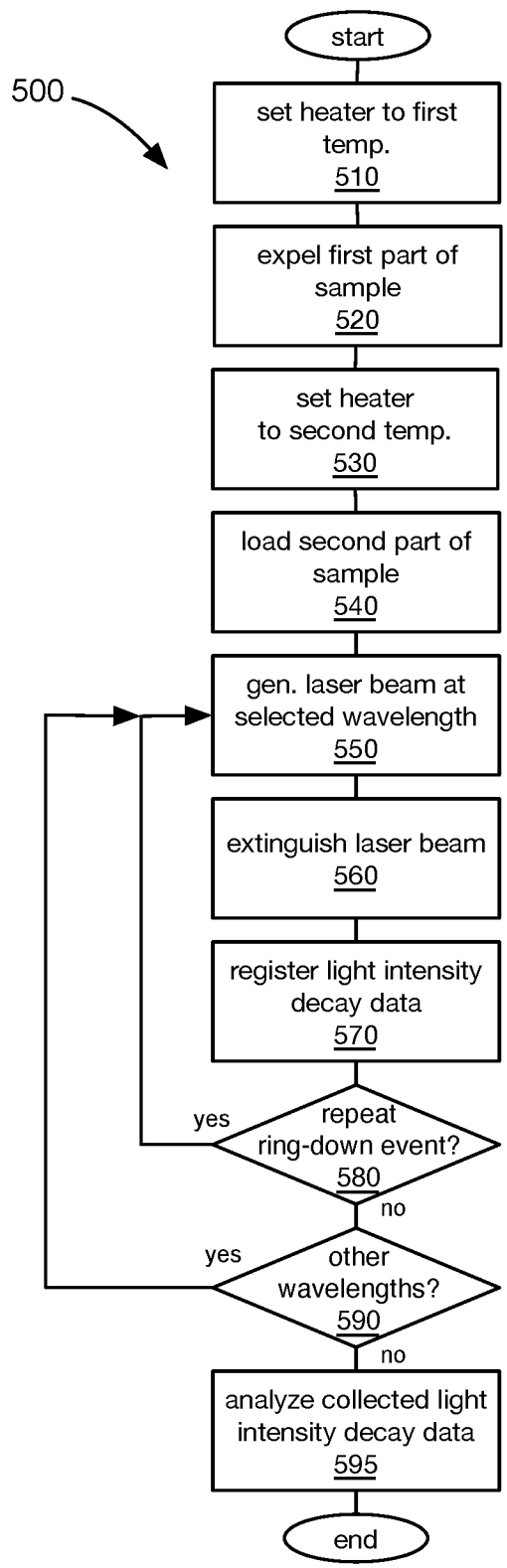
FIG. 6 shows a method of analyzing light intensity decay data for a sample using the CRDS system of FIG. 1 in accordance with another embodiment.

FIG. 6 shows a method 500 of analyzing a sample via CRDS. In the method 500, a part of the sample is desorbed at a first temperature and is, in effect, discarded as it may have little correlation to the presence or absence of a physiological condition in a patient. A second part of the sample is desorbed at a second temperature. The second part of the sample is deemed to have a relatively high correlation to the presence of the physiological condition or a degree of the physiological condition and is thus analyzed via CRDS.

The method 500 commences with the setting of the temperature of the heater 132 at a first desorption temperature by the control module 204 (510). Heating of the heater 132 to the first desorption temperature causes the thermal desorption tube 104 to be heated and a first part of the sample to be desorbed. The sample-loading system 112 is then directed by the control module 204 to expel the first part of the sample without performing CRDS on the first part. The first part of the sample may be expelled to the surrounding atmosphere, to a collection canister, or may be removed from the path between the thermal desorption tube 104 and the ring-down cavity 84 via any other suitable approach. In a presently preferred embodiment, the first sample is expelled through the mass flow controller 136 by closing valves 124*b* and 124*d*, and by opening valves 124*a*, 124*c*, 124*g*, 124*f*, and 124*h*, much in the same manner that carbon dioxide and water are expelled from the thermal desorption tube 104.

After expelling the first part of the sample, the heater is heated to a second desorption temperature (530). The second desorption temperature is generally higher than the first temperature and, as a result, causes different substances to be desorbed from the thermal desorption tube 104. In other embodiments, the second desorption temperature is the same as or lower than the first desorption temperature. While a good portion of some components/compounds may have already been desorbed at the previous desorption temperature, virtually all of other confounding substances may have been desorbed as well, thus facilitating the isolation of these components/compounds. The second part of the sample is then loaded into the ring-down cavity 84 for analysis, as described above (540). Next, the control module 204 operates one of the lasers 24, 28 to generate a laser beam at a selected wavelength (550). The laser beam is directed into the ring-down cavity 84 to fill the cavity with light. Once the ring-down cavity 84 is filled, the laser beam is extinguished (560). The liquid nitrogen-cooled detector 100 then registers the intensity of the light exiting the ring-down cavity 84 via the rear cavity mirror 88*b* (570). The light exiting the ring-down cavity 84 represents light intensity decay data that is registered by the liquid nitrogen-cooled detector 100 and transmitted to the control module 204.

Once the ring-down event is complete, it is determined whether to repeat the ring-down event again (580). As noted above, it can be desirable to repeat the ring-down event a number of times and then determine one or more collective metrics by determining a decay rate for the light intensity decay data for each ring-down and then averaging the decay rates to minimize the effect of aberrations. If another ring-down event is to be repeated, a laser beam is generated at the selected wavelength at 550. If, instead, no more ring-down events are to be performed, it is determined whether there are other wavelengths in the set of wavelengths to be analyzed (590). If it is determined that there are other wavelengths to be analyzed, a laser beam of a next one of the wavelengths is generated at 550. If, instead, there are no more wavelengths to generate a laser beam at for performing CRDS, the light intensity decay data collected at 570 is then analyzed (595), after which the method 500 ends. The collected light intensity decay data is then analyzed.

While the at least one processor that analyzes the light intensity decay data and generates a predictive model is shown and described as being fully integrated with the other elements of the CRDS system, in other embodiments, one or more of the at least one processor can be provided in a separate computer system that has storage and performs some or all of the functionality of the control module in the above-described and illustrated embodiment.

Figure 7A:
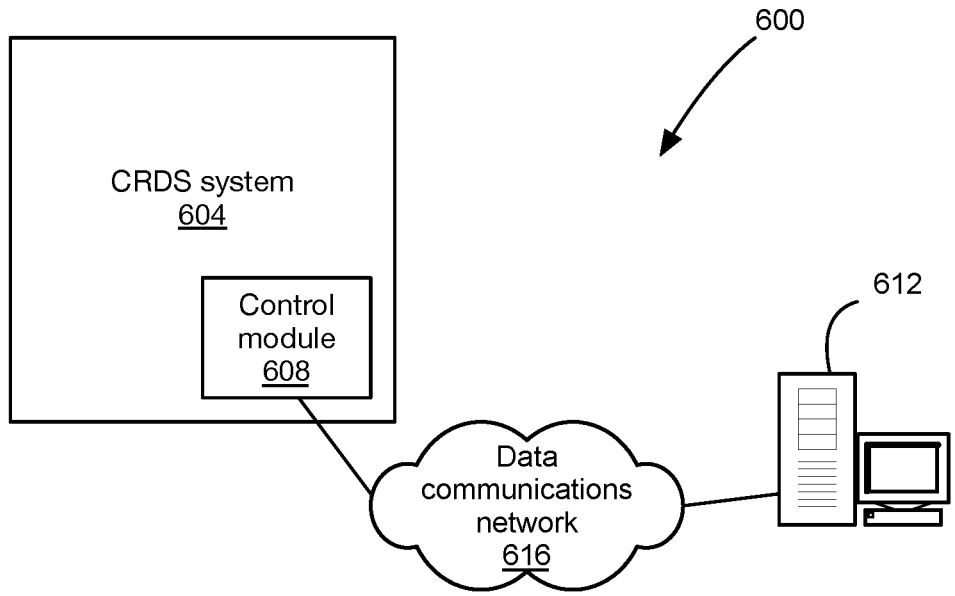
FIG. 7A shows a CRDS analysis system in accordance with another embodiment, wherein a computing device is in communication with the CRDS system.

FIG. 7A shows a system 600 for analyzing a sample using CRDS in another embodiment. The system 600 includes a CRDS system 604 similar to that of FIG. 1. The CRDS system 604 has a control module 608 that has at least one processor for controlling operation of the various elements of the CRDS system 604. The control module 608 is in communication with a computer system 612 over a data communications network 616. The computer system 612 can be any single computer or multiple computers coupled together locally and/or remotely to provide the described functionality. The data communications network 616 can be any suitable medium enabling the control module 608 and the computer system 612 to communicate at least the light intensity decay data and any associated parameters associated therewith, such as wavelengths, the temperature at which the at least part of the sample was desorbed, as well as any other subject-specific data, such as the above-noted confounding factors, a subject identifier, time and location information for when and where the sample was analyzed, etc.

Figure 7B:
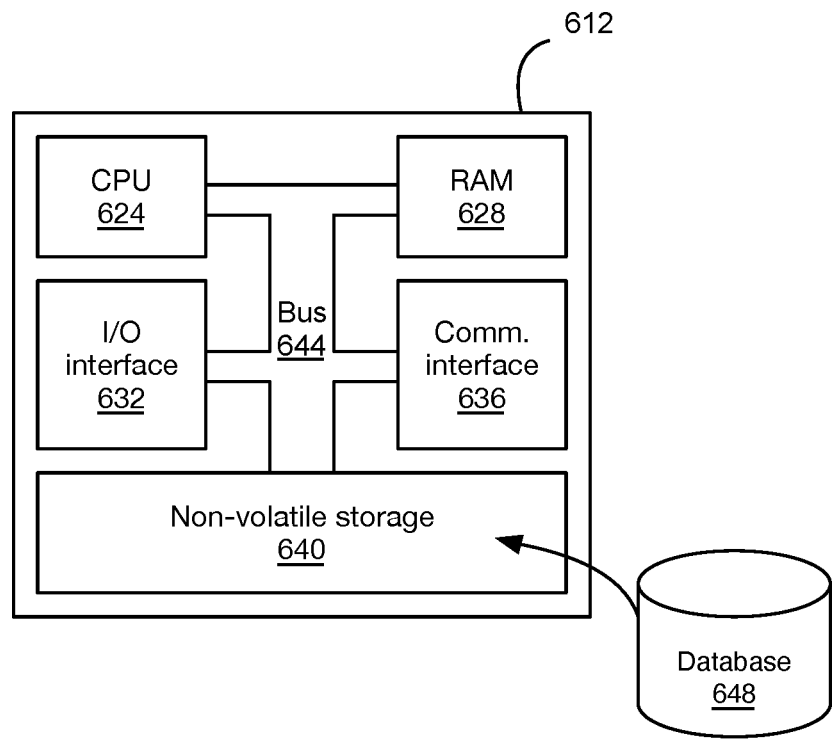
FIG. 7B is a schematic diagram of the computing device of FIG. 7A.

FIG. 7B shows a number of physical and logical components of the computer system 612, including a central processing unit ("CPU") 624, random access memory ("RAM") 628, an input/output ("I/O") interface 632, a communications interface 636, non-volatile storage 640, and a local bus 644 enabling the CPU 624 to communicate with the other components. The CPU 624 can include one or more processors and executes at least an operating system, as well as a spectra evaluation application. The RAM 628 provides relatively responsive volatile storage to the CPU 624. The I/O interface 632 allows for input to be received from one or more devices, such as a keyboard, a mouse, etc., and outputs information to output devices, such as a display and/or speakers. The communications interface 636 permits communication with other computing devices like the control module 608 over computer networks such as the data communications network 616. The non-volatile storage 640 stores the operating system and programs, including computer-executable instructions for implementing the spectra evaluation application. During operation of the computer system 612, the operating system, the programs and the data may be retrieved from the non-volatile storage 640 and placed in RAM 628 to facilitate execution.

While, in the above-described embodiment, the light sources are two lasers that produce light in the mid-infrared range, it will be appreciated that other light sources can be employed. For example, a laser producing light in the visible spectrum or a near-infrared laser can be employed. Further, in some scenarios, the CRDS system can include only one laser, or three or more lasers, to generate the working beam.

Electro-optic modulators can be used in place of acousto-optic modulators.

The acousto-optic modulators can be configured so that the frequency of the working beam is shifted up or down. As long as the net frequency shift effected by the acousto-optic modulators shifts the frequency of the working beam significantly away from the frequency of the working beam being generated by the laser(s) so that the reflected light is outside of the bandwidth of the laser light being generated, the amount of interference between the reflected light and the generated working beam can be minimized.

In other embodiments, more than two optical modulators can be employed in a CRDS system to provide further extinguishing capacity to more quickly extinguish the working beam at the commencement of a ring-down event. Further, in further embodiments, a single optical modulator can be employed.

One or more focusing lenses can be employed in other embodiments, and translated to enable repositioning of the lenses to allow mode-matching of each wavelength of the lasers.

The same approach can be adopted for other types of resonant cavities, and particularly optical resonant cavities.

Other types of events can be triggered as the cavity length is proximal to the resonance length of the cavity for the particular selected wavelength.

Analysis of the samples can be performed at pressure levels other than one atmosphere in other embodiments. The breadth of the absorption spectrum may change accordingly.

Although specific advantages have been enumerated above, various embodiments may include some, none, or all of the enumerated advantages.

While, in the above-described embodiment, the resonant cavity is a ring-down cavity, in other embodiments, other types of resonant cavities can be employed.

Persons skilled in the art will appreciate that there are yet more alternative implementations and modifications possible, and that the above examples are only illustrations of one or more implementations. The scope, therefore, is only to be limited by the claims appended hereto.

LIST OF REFERENCE NUMERALS

20 CRDS system
24 CO2 laser
28 carbon-13 O2 laser
32 first laser beam
36 second laser beam
40 mirror
44 beam splitter
48 sampling beam
52 output beam
56 fast infrared detector
60 first optical modulator
64 mirror
68 second optical modulator
72 focusing lens
76 mirror
80 ring-down chamber
84 ring-down cavity
88 cavity mirror
88a front cavity mirror
88b rear cavity mirror
92 mirror mounts
96 micrometer
96a mechanized micrometer
96b piezoelectric micrometer
100 liquid nitrogen-cooled detector
104 thermal desorption tube 105 stainless-steel casing
106 aperture
107 receiving end
108 foam separator
109 sorbent material
110 foam separator
112 sample-loading system
116 nitrogen gas source
120 conduit
120a gas intake line
120b desorption tube line
120c sample outlet line
124 solenoid valve
124a gas inlet valve
124b auxiliary gas inlet valve
124c gas intake line valve
124d cavity inlet valve
124e pathing valve
124f forward valve
124g rearward valve
124h sample outlet valve
124i cavity outlet valve
124j vacuum cutoff valve
124k vacuum intake valve
128 pressure meter
130a, 130b filter
132 heater
136 mass flow controller
140 outlet line
144 pressure meter
148 vacuum pump
150 pump intake line
200 electronic control subsystem
204 control module
205 processor
206 storage
208 RF driver
212 grating actuator
216 output coupler piezo
220 high-voltage amplifier
224 DAQ card
228 actuator driver
232 amplifier
236 oscilloscope
240 temperature controller
244 relay board
248 three-channel piezo driver
252 piezo actuator
256 RF driver
260 timing circuit
264 digitizer
RL resonance length
300 method
310 select and set temperature
320 load at least part of sample
330 generate laser beam at selected wavelength
340 extinguish laser beam
350 registering light intensity decay data
360 repeat ring-down event?
370 other wavelengths?
375 unload sample part
380 other temps. in seq.?
390 determine probability of physiological condition
400 method
404 select sample
408 select temperature sequence
412 set heater temperature
416 load a part of sample
420 generate laser beam at wavelength
424 extinguish laser beam
428 register light intensity decay data
430 repeat ring-down event?
432 other wavelengths?
436 other temperatures?
436 determine probability of physiological condition
440 other temperature sequence?
444 other samples?
448 identify temperature sequence with greater correlation
452 select temperature sequence
456 generate predictive model
500 method
510 set heater to first temperature
520 expel first part of sample
530 set heater to second temperature
540 load second part of sample
550 generate laser beam at selected wavelength
560 extinguish laser beam
570 register light intensity decay data
580 repeat ring-down event?
590 other wavelengths?
595 analyze collected light intensity decay data
600 system
604 CRDS system
608 control module
612 computer system
616 data communications network
624 processor
628 RAM
632 I/O interface
636 communications interface
640 non-volatile storage
644 bus
648 database

What is claimed is:

1. A method for analyzing a sample using cavity ring-down spectroscopy, comprising:
desorbing a first part of a breath sample from a thermal desorption tube heated to a first desorption temperature to load the first part of the breath sample into a ring-down cavity;
for each of a first set of wavelengths:
generating, via at least one laser, a laser beam at the wavelength directed into the ring-down cavity;
extinguishing the laser beam entering the ring-down cavity; and
registering light intensity decay data for light exiting the ring-down cavity via a light intensity sensor system;
loading a second part of the sample desorbed from the thermal desorption tube heated to a second desorption temperature;
for each of a second set of wavelengths:
generating, via at least one laser, a laser beam at the wavelength directed into the ring-down cavity;
extinguishing the laser beam entering the ring-down cavity; and
registering light intensity decay data for light exiting the ring-down cavity via a light intensity sensor system; and
determining, via at least one processor, a probability from the light intensity decay data using a predictive model that is at least partially based on the dataset of light intensity decay data for the first set of wavelengths and the second set of wavelengths that a subject from which the breath sample was received has a physiological condition or a degree of a physiological condition at least indirectly using a dataset of light intensity decay data for previously analyzed breath samples for which the presence or absence of lung cancer or the degree of lung cancer has been identified.

2. The method of claim 1, wherein the second set of wavelengths is equal to the first set of wavelengths.

3. The method of claim 2, further comprising:
combining the light intensity decay data from the second part of the sample to the light intensity decay data from the first part of the sample for each of the first set of wavelengths.

4. The method of claim 1, wherein the determining is performed using a predictive model trained at least partially using the dataset of light intensity decay data for previously analyzed samples.

5. The method of claim 1, wherein the generating, the extinguishing, and the registering are performed until a control module determines that a desired level of light intensity decay data has been collected.

6. A system for analyzing a sample using cavity ring-down spectroscopy, comprising:
a ring-down cavity;
at least one laser operable to generate a laser beam at each of a first set of wavelengths, the laser beam being directed into the ring-down cavity;
a sample-loading system for loading a first part of a breath sample from a thermal desorption tube into the ring-down cavity for analysis, and for unloading the first part of the breath sample from the ring-down cavity;
a light intensity sensor system positioned to register light intensity decay data for light exiting the ring-down cavity;
at least one processor operably coupled to the sample-loading system, the at least one laser, and the light intensity sensor system;
a storage storing computer-readable instructions that, when executed by the at least one processor, cause the at least one processor to:
control the sample-loading system to desorb the first part of the breath sample by heating the thermal desorption tube to a first desorption temperature to load the first part of the breath sample into the ring-down cavity;
for each of the first set of wavelengths:
operate the at least one laser to generate the laser beam directed into the ring-down cavity;
extinguish the laser beam entering the ring-down cavity; and
register light intensity decay data for light exiting the ring-down cavity via the light intensity sensor system;
control the sample-loading system to desorb a second part of the sample by heating the thermal desorption tube to a second desorption temperature to load the second part of the sample into the ring-down cavity after unloading the first part of the sample from the ring-down cavity,
for each of a second set of wavelengths:
operate the at least one laser to generate the laser beam directed into the ring-down cavity;
extinguish the laser beam entering the ring-down cavity; and
register light intensity decay data for light exiting the ring-down cavity via the light intensity sensor system; and determine a probability from the light intensity decay data for the first set of wavelengths that a subject from which the breath sample was received has a physiological condition or a degree of a physiological condition at least indirectly using a predictive model that is at least partially based on a dataset of light intensity decay data for previously analyzed breath samples for which the presence or absence of the physiological condition or the degree of the physiological condition has been identified.

7. The system of claim 6, wherein the second set of wavelengths is equal to the first set of wavelengths.

8. The system of claim 7, wherein the at least one processor combines the light intensity decay data from the second part of the sample to the light intensity decay data to the first part of the sample for each of the first set of wavelengths.

9. The system of claim 6, wherein the at least one processor determines the probability from the light intensity decay data using a predictive model trained at least partially using the dataset of light intensity decay data for previously analyzed samples.

10. The system of claim 6, wherein the at least one processor repeats the operating extinguishing, and registering until the at least one processor determines that a desired level of light intensity decay data has been collected.

11. A method for analyzing a sample using cavity ring-down spectroscopy, comprising:
heating a thermal desorption tube to a first desorption temperature to desorb a first part of a sample contained therein;
loading the first part of the sample into a ring-down cavity;
for each of a first set of wavelengths:
generating, via at least one laser, a laser beam at the wavelength that is directed into the ring-down cavity;
extinguishing the laser beam entering the cavity; and
registering light intensity decay data for light exiting the ring-down cavity via a light intensity sensor system;
unloading the first part of the sample from the ring-down cavity;
heating the thermal desorption tube to a second desorption temperature to desorb a second part of the sample contained therein;
loading the second part of the sample into the ring-down cavity;
for each of a second set of wavelengths:
generating, via the at least one laser, a laser beam at the wavelength that is directed into the ring-down cavity;
extinguishing the laser beam entering the cavity; and
registering light intensity decay data for light exiting the ring-down cavity via the light intensity sensor system; and
analyzing the light intensity decay data desorbed at the first desorption temperature and the light intensity decay data desorbed at the second desorption temperature to detect a probability that a subject from which the sample was received has a physiological condition or a degree of a physiological condition.

12. The method of claim 11, wherein the first set of wavelengths is equal to the second set of wavelengths.

13. The method of claim 12, further comprising:
combining the light intensity decay data from the second part of the sample to the light intensity decay data from the first part of the sample for each of the first set of wavelengths.

14. The method of claim 11, wherein the second desorption temperature is greater than the first desorption temperature.

15. The method of claim 11, wherein the first desorption temperature is equal to the second desorption temperature.

16. The method of claim 11, wherein the analyzing comprises determining a probability from the light intensity decay data for the first part of the sample and the light intensity decay data for the second part of the sample that a subject from which the sample was received has a physiological condition or a degree of the physiological condition at least indirectly using a dataset of light intensity decay data for previously analyzed samples for which the presence or absence of the physiological condition or the degree of the physiological condition has been identified.

17. The method of claim 16, wherein the determining is performed using a predictive model trained at least partially using the dataset of light intensity decay data for previously analyzed samples.

* * * * *